(12) United States Patent
Austin et al.

(10) Patent No.: US 8,105,367 B2
(45) Date of Patent: Jan. 31, 2012

(54) BONE PLATE AND BONE PLATE ASSEMBLIES INCLUDING POLYAXIAL FASTENERS

(75) Inventors: Gene Edward Austin, Bartlett, TN (US); Brian L. Black, Southave, MS (US); Sied W. Janna, Memphis, TN (US); Timothy J. Petteys, Bartlett, TN (US); James K. Rains, Cordova, TN (US); John B. Schneider, Memphis, TN (US); Jon A. Harmon, Byhalia, MS (US); Darin S. Gerlach, Germantown, TN (US); Anthony H. James, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 103 days.

(21) Appl. No.: 12/484,527

(22) Filed: Jun. 15, 2009

(65) Prior Publication Data

US 2009/0312803 A1 Dec. 17, 2009

Related U.S. Application Data

(63) Continuation-in-part of application No. 11/644,306, filed on Dec. 22, 2006, which is a continuation of application No. 10/673,833, filed on Sep. 29, 2003, now Pat. No. 7,179,260, application No. 12/484,527, which is a continuation-in-part of application No. 11/996,795, filed as application No. PCT/US2006/028778 on Jul. 25, 2006.

(60) Provisional application No. 60/702,231, filed on Jul. 25, 2005.

(51) Int. Cl.
*A61B 17/80* (2006.01)

(52) U.S. Cl. .................................................. 606/280

(58) Field of Classification Search .................. 606/281, 606/280, 286, 301, 305, 290, 71, 289, 86 R
See application file for complete search history.

(56) References Cited

U.S. PATENT DOCUMENTS 300,146 A   6/1884   Sinnett
(Continued)

FOREIGN PATENT DOCUMENTS

AU   754857   11/2002
(Continued)

OTHER PUBLICATIONS

Smith & Nephew Brochure entitled 'Surgical Technique PERI-LOC VLP Variable-Angle Locked Plating System,' pp. 1-32 (Nov. 2007).

(Continued)

*Primary Examiner* — Pedro Philogene
(74) *Attorney, Agent, or Firm* — Fish & Richardson P.C.

(57) ABSTRACT

A system for fixation of bone, including a bone plate with an opening comprising threads made of a first material and a fastener with a head at least partially comprising a polymeric material that is softer than the first material. In some embodiments, when the fastener is inserted into the first opening, the threads of the first opening form threads in the polymeric material on the head of the fastener and secure the fastener in place at one of a plurality of possible angles within the first opening. The first opening additionally accepts a fastener with a substantially spherical head for compression of a fracture, or a fastener with a threaded head that engages with the threads of the threaded opening. In some embodiments the first opening includes a substantially frustoconical-shaped top portion. In other embodiments there may be a second opening that is either non-threaded or comprises a plurality of protruding fins.

26 Claims, 30 Drawing Sheets

U.S. PATENT DOCUMENTS

| | | |
|---|---|---|
| 351,751 A | 11/1886 | Douglas |
| 382,670 A | 5/1888 | Trovillion |
| 544,606 A | 8/1895 | Balsley |
| 545,331 A | 8/1895 | Balsley |
| 565,808 A | 8/1896 | Staples |
| 575,631 A | 1/1897 | Brooks |
| 583,158 A | 5/1897 | Upham |
| 637,990 A | 11/1899 | Hoepner |
| 651,949 A | 6/1900 | Lillie |
| 689,722 A | 12/1901 | Hoover |
| 766,270 A | 8/1904 | Lapham |
| 775,427 A | 11/1904 | Lusted, Sr. |
| 902,040 A | 10/1908 | Wyckoff |
| 1,025,008 A | 4/1912 | Miner |
| 1,105,105 A | 7/1914 | Sherman |
| 1,275,810 A | 8/1918 | White |
| 1,575,149 A | 3/1928 | Craig et al. |
| 1,755,588 A | 4/1930 | Bronk |
| 1,925,385 A | 9/1933 | Humes et al. |
| 2,010,913 A * | 8/1935 | Bruce et al. .................. 408/221 |
| 2,133,859 A | 10/1938 | Hawley et al. |
| 2,152,977 A | 4/1939 | Schindel |
| 2,388,921 A | 11/1945 | Sutter et al. |
| 2,501,978 A | 3/1950 | Wichman |
| 2,524,167 A | 10/1950 | Grande |
| 2,560,912 A | 7/1951 | Aitto |
| 2,667,194 A | 1/1954 | Fischer et al. |
| 2,756,791 A | 7/1956 | Ferrara |
| 3,056,441 A | 10/1962 | Helms |
| 3,279,510 A | 10/1966 | Dreyer et al. |
| 3,347,293 A | 10/1967 | Clark |
| 3,409,058 A | 11/1968 | LaPointe |
| 3,547,114 A | 12/1970 | Haboush |
| 3,552,389 A | 1/1971 | Allgower et al. |
| 3,630,261 A | 12/1971 | Gley |
| 3,662,797 A | 5/1972 | Healis |
| 3,668,972 A | 6/1972 | Allgower et al. |
| 3,716,050 A | 2/1973 | Johnston |
| 3,739,825 A | 6/1973 | Knox |
| 3,741,205 A | 6/1973 | Markolf et al. |
| 3,744,488 A | 7/1973 | Cox |
| 3,779,240 A | 12/1973 | Kondo |
| 3,782,432 A | 1/1974 | Allen |
| 3,866,607 A | 2/1975 | Forsythe et al. |
| 3,906,550 A | 9/1975 | Rostoker et al. |
| 3,935,762 A | 2/1976 | Tudisco |
| RE28,841 E | 6/1976 | Allgower et al. |
| 4,059,102 A | 11/1977 | Devas |
| 4,060,114 A | 11/1977 | Matsushima |
| 4,096,896 A | 6/1978 | Engel |
| 4,219,015 A | 8/1980 | Steinemann |
| 4,246,811 A | 1/1981 | Bondhus et al. |
| 4,263,904 A | 4/1981 | Juder |
| 4,338,926 A | 7/1982 | Kummer et al. |
| 4,364,382 A | 12/1982 | Menen |
| 4,388,921 A | 6/1983 | Sutter et al. |
| 4,408,601 A | 10/1983 | Wenk |
| RE31,628 E | 7/1984 | Allgower et al. |
| 4,484,570 A | 11/1984 | Sutter et al. |
| 4,493,317 A | 1/1985 | Klaue |
| 4,513,744 A | 4/1985 | Klaue |
| 4,535,658 A | 8/1985 | Molinari |
| 4,564,007 A | 1/1986 | Coombs et al. |
| 4,565,193 A | 1/1986 | Streli |
| 4,573,458 A | 3/1986 | Lower |
| 4,683,878 A | 8/1987 | Carter |
| 4,704,929 A | 11/1987 | Osada |
| 4,794,918 A | 1/1989 | Wolter |
| 4,838,252 A | 6/1989 | Klaue |
| 4,927,421 A | 5/1990 | Goble et al. |
| 4,978,349 A | 12/1990 | Frigg |
| 4,988,350 A | 1/1991 | Herzberg |
| 5,002,544 A | 3/1991 | Klaue et al. |
| 5,006,120 A | 4/1991 | Carter |
| 5,041,114 A | 8/1991 | Chapman et al. |
| 5,053,036 A | 10/1991 | Perrin et al. |
| 5,085,660 A | 2/1992 | Lin |
| 5,129,901 A | 7/1992 | Decoste |
| 5,151,103 A | 9/1992 | Tepic et al. |
| 5,190,544 A | 3/1993 | Chapman et al. |
| 5,192,281 A | 3/1993 | de la Caffiniere |
| 5,197,966 A | 3/1993 | Sommerkamp |
| 5,198,308 A | 3/1993 | Shetty et al. |
| 5,237,893 A | 8/1993 | Ryder et al. |
| 5,259,398 A | 11/1993 | Vrespa |
| 5,269,784 A | 12/1993 | Mast |
| 5,275,601 A | 1/1994 | Gogolewski et al. |
| 5,304,180 A | 4/1994 | Slocum |
| 5,312,410 A | 5/1994 | Miller et al. |
| 5,324,290 A | 6/1994 | Zdeblick et al. |
| 5,324,291 A | 6/1994 | Ries et al. |
| 5,356,410 A | 10/1994 | Pennig |
| 5,360,452 A | 11/1994 | Engelhardt et al. |
| 5,364,398 A | 11/1994 | Chapman et al. |
| 5,364,399 A | 11/1994 | Lowery et al. |
| 5,395,374 A | 3/1995 | Miller et al. |
| 5,415,658 A | 5/1995 | Kilpela et al. |
| 5,423,820 A | 6/1995 | Miller et al. |
| 5,423,826 A | 6/1995 | Coates et al. |
| 5,429,641 A | 7/1995 | Gotfried |
| 5,431,659 A | 7/1995 | Ross, Jr. et al. |
| 5,470,333 A | 11/1995 | Ray |
| 5,474,553 A | 12/1995 | Baumgart |
| 5,487,743 A | 1/1996 | Laurain et al. |
| 5,514,138 A | 5/1996 | McCarthy |
| 5,520,690 A | 5/1996 | Errico et al. |
| 5,522,902 A | 6/1996 | Yuan et al. |
| 5,527,310 A | 6/1996 | Cole et al. |
| 5,531,143 A | 7/1996 | Habermehl et al. |
| 5,531,746 A | 7/1996 | Errico et al. |
| 5,531,748 A | 7/1996 | de la Caffiniere |
| 5,534,032 A | 7/1996 | Hodorek |
| 5,536,127 A | 7/1996 | Pennig |
| 5,569,253 A | 10/1996 | Farris et al. |
| 5,578,034 A | 11/1996 | Estes |
| 5,591,168 A | 1/1997 | Judet et al. |
| 5,601,553 A | 2/1997 | Trebing et al. |
| 5,607,426 A | 3/1997 | Ralph |
| 5,607,428 A | 3/1997 | Lin |
| 5,643,265 A | 7/1997 | Errico |
| 5,647,873 A | 7/1997 | Errico et al. |
| 5,665,088 A | 9/1997 | Gil et al. |
| 5,665,089 A | 9/1997 | Dall et al. |
| 5,676,667 A | 10/1997 | Hausman |
| 5,702,399 A | 12/1997 | Kilpela et al. |
| 5,709,686 A | 1/1998 | Talos et al. |
| 5,713,900 A | 2/1998 | Benzel et al. |
| 5,725,588 A | 3/1998 | Errico et al. |
| 5,733,287 A | 3/1998 | Tepic et al. |
| 5,735,853 A | 4/1998 | Olerud |
| 5,741,258 A | 4/1998 | Klaue et al. |
| 5,749,872 A | 5/1998 | Kyle et al. |
| 5,769,850 A | 6/1998 | Chin |
| 5,772,662 A | 6/1998 | Chapman et al. |
| 5,776,196 A | 7/1998 | Matsuzaki et al. |
| 5,788,697 A | 8/1998 | Kilpela et al. |
| 5,797,912 A | 8/1998 | Runciman et al. |
| 5,810,823 A | 9/1998 | Klaue et al. |
| 5,824,247 A | 10/1998 | Tunc |
| 5,876,402 A | 3/1999 | Errico |
| 5,888,204 A | 3/1999 | Ralph |
| 5,893,856 A | 4/1999 | Jacob et al. |
| 5,902,305 A | 5/1999 | Beger et al. |
| 5,904,683 A | 5/1999 | Pohndorf |
| 5,904,684 A | 5/1999 | Rooks |
| 5,925,047 A | 7/1999 | Errico et al. |
| 5,935,130 A | 8/1999 | Kipela et al. |
| 5,935,133 A | 8/1999 | Wagner et al. |
| 5,938,664 A | 8/1999 | Winquist et al. |
| 5,954,722 A | 9/1999 | Bono |
| 5,960,681 A | 10/1999 | Anderson et al. |
| 5,961,524 A | 10/1999 | Crombie |
| 5,964,769 A | 10/1999 | Wagner et al. |
| 5,968,046 A | 10/1999 | Castleman |
| 5,968,047 A | 10/1999 | Reed |
| 5,976,141 A | 11/1999 | Haag et al. |
| 6,016,727 A | 1/2000 | Morgan |

| | | | |
|---|---|---|---|
| 6,019,762 A | 2/2000 | Cole | |
| 6,022,352 A | 2/2000 | Vandewalle | |
| 6,053,921 A | 4/2000 | Wagner et al. | |
| 6,096,040 A | 8/2000 | Esser | |
| 6,129,730 A | 10/2000 | Bono et al. | |
| 6,176,861 B1 | 1/2001 | Bernstein et al. | |
| 6,183,475 B1 | 2/2001 | Lester et al. | |
| 6,193,721 B1 | 2/2001 | Michelson | |
| 6,206,881 B1 * | 3/2001 | Frigg et al. | 606/291 |
| 6,214,049 B1 | 4/2001 | Gayer et al. | |
| 6,228,085 B1 | 5/2001 | Theken et al. | |
| 6,235,033 B1 | 5/2001 | Brace | |
| RE37,249 E | 6/2001 | Leibinger et al. | |
| 6,258,092 B1 | 7/2001 | Dall | |
| 6,273,889 B1 | 8/2001 | Richelsoph | |
| 6,302,001 B1 | 10/2001 | Karle | |
| 6,302,883 B1 | 10/2001 | Bono | |
| 6,306,136 B1 | 10/2001 | Baccelli | |
| 6,306,140 B1 | 10/2001 | Siddiqui | |
| 6,309,393 B1 | 10/2001 | Tepic et al. | |
| 6,322,562 B1 | 11/2001 | Wolter | |
| 6,342,055 B1 | 1/2002 | Eisermann et al. | |
| 6,355,041 B1 | 3/2002 | Martin et al. | |
| 6,355,043 B1 | 3/2002 | Adam | |
| 6,358,250 B1 | 3/2002 | Orbay | |
| 6,361,537 B1 | 3/2002 | Anderson | |
| 6,364,885 B1 | 4/2002 | Kilpela et al. | |
| 6,379,359 B1 | 4/2002 | Dahners | |
| 6,391,030 B1 | 5/2002 | Wagner et al. | |
| 6,413,259 B1 | 7/2002 | Lyons et al. | |
| 6,428,542 B1 | 8/2002 | Michelson | |
| 6,436,100 B1 | 8/2002 | Berger | |
| 6,440,135 B2 | 8/2002 | Orbay et al. | |
| 6,454,769 B2 | 9/2002 | Wagner | |
| 6,454,770 B1 | 9/2002 | Klaue | |
| 6,468,278 B1 | 10/2002 | Muckter | |
| 6,475,218 B2 | 11/2002 | Gournay et al. | |
| 6,506,191 B1 | 1/2003 | Joos | |
| 6,520,965 B2 | 2/2003 | Chervitz et al. | |
| 6,524,238 B2 | 2/2003 | Velikaris et al. | |
| 6,527,776 B1 | 3/2003 | Michelson | |
| 6,558,387 B2 | 5/2003 | Errico | |
| 6,575,975 B2 | 6/2003 | Brace et al. | |
| 6,595,993 B2 | 7/2003 | Donno et al. | |
| 6,595,994 B2 | 7/2003 | Kilpela et al. | |
| 6,605,090 B1 | 8/2003 | Trieu et al. | |
| 6,623,486 B1 * | 9/2003 | Weaver et al. | 606/281 |
| 6,669,700 B1 | 12/2003 | Farris et al. | |
| 6,669,701 B2 | 12/2003 | Steiner et al. | |
| 6,682,533 B1 | 1/2004 | Dinsdale et al. | |
| 6,684,741 B2 | 2/2004 | Blackston | |
| 6,689,133 B2 | 2/2004 | Morrison et al. | |
| 6,719,759 B2 | 4/2004 | Wagner et al. | |
| 6,730,091 B1 * | 5/2004 | Pfefferle et al. | 606/70 |
| 6,755,829 B1 | 6/2004 | Bono | |
| 6,767,351 B2 | 7/2004 | Orbay et al. | |
| 6,780,186 B2 | 8/2004 | Errico | |
| 6,821,278 B2 | 11/2004 | Frigg et al. | |
| 6,866,665 B2 | 3/2005 | Orbay | |
| 6,893,443 B2 | 5/2005 | Frigg et al. | |
| 6,893,444 B2 | 5/2005 | Orbay | |
| 6,916,320 B2 | 7/2005 | Michelson | |
| 6,945,975 B2 | 9/2005 | Dalton | |
| 6,955,677 B2 * | 10/2005 | Dahners | 606/287 |
| 6,960,213 B2 | 11/2005 | Chervitz et al. | |
| 6,969,390 B2 | 11/2005 | Michelson | |
| 6,973,860 B2 | 12/2005 | Nish | |
| 6,974,461 B1 | 12/2005 | Wolter | |
| 6,979,334 B2 | 12/2005 | Dalton | |
| 7,073,415 B2 | 7/2006 | Casutt et al. | |
| 7,074,221 B2 | 7/2006 | Michelson | |
| 7,128,744 B2 | 10/2006 | Weaver et al. | |
| 7,172,593 B2 | 2/2007 | Trieu et al. | |
| 7,179,260 B2 | 2/2007 | Gerlach et al. | |
| 7,230,039 B2 | 6/2007 | Trieu et al. | |
| 7,250,053 B2 | 7/2007 | Orbay | |
| 7,250,054 B2 | 7/2007 | Allen et al. | |
| 7,255,701 B2 | 8/2007 | Allen et al. | |
| 7,282,053 B2 | 10/2007 | Orbay | |
| 7,294,130 B2 | 11/2007 | Orbay | |
| 7,341,589 B2 | 3/2008 | Weaver et al. | |
| 7,419,714 B1 | 9/2008 | Magerl et al. | |
| 7,695,472 B2 | 4/2010 | Young | |
| 7,766,948 B1 * | 8/2010 | Leung | 606/305 |
| 2001/0037112 A1 | 11/2001 | Brace et al. | |
| 2001/0047174 A1 | 11/2001 | Donno et al. | |
| 2002/0013587 A1 | 1/2002 | Winquist et al. | |
| 2002/0045901 A1 | 4/2002 | Wagner et al. | |
| 2002/0058940 A1 | 5/2002 | Frigg et al. | |
| 2002/0058943 A1 | 5/2002 | Kilpela et al. | |
| 2002/0115742 A1 | 8/2002 | Trieu et al. | |
| 2002/0143338 A1 | 10/2002 | Orbay et al. | |
| 2002/0161370 A1 | 10/2002 | Frigg et al. | |
| 2003/0040749 A1 | 2/2003 | Grabowski et al. | |
| 2003/0057590 A1 | 3/2003 | Loher et al. | |
| 2003/0060827 A1 | 3/2003 | Coughln | |
| 2003/0105462 A1 | 6/2003 | Haider | |
| 2003/0183335 A1 | 10/2003 | Winniczek et al. | |
| 2004/0010257 A1 | 1/2004 | Cachia et al. | |
| 2004/0030342 A1 | 2/2004 | Trieu et al. | |
| 2004/0044345 A1 | 3/2004 | DeMoss et al. | |
| 2004/0059334 A1 | 3/2004 | Weaver et al. | |
| 2004/0059335 A1 | 3/2004 | Weaver et al. | |
| 2004/0073218 A1 | 4/2004 | Dahners | |
| 2004/0087954 A1 | 5/2004 | Allen et al. | |
| 2004/0097942 A1 | 5/2004 | Allen et al. | |
| 2004/0138666 A1 | 7/2004 | Molz, IV et al. | |
| 2004/0181228 A1 | 9/2004 | Wagner et al. | |
| 2004/0199169 A1 | 10/2004 | Koons et al. | |
| 2004/0215195 A1 | 10/2004 | Shipp et al. | |
| 2004/0220570 A1 | 11/2004 | Frigg | |
| 2004/0236332 A1 | 11/2004 | Frigg | |
| 2004/0260306 A1 | 12/2004 | Fallin et al. | |
| 2005/0010220 A1 | 1/2005 | Casutt et al. | |
| 2005/0010226 A1 | 1/2005 | Grady, Jr. et al. | |
| 2005/0043736 A1 | 2/2005 | Mathieu et al. | |
| 2005/0049593 A1 | 3/2005 | Duong et al. | |
| 2005/0070904 A1 | 3/2005 | Gerlach et al. | |
| 2005/0080421 A1 | 4/2005 | Weaver et al. | |
| 2005/0107796 A1 | 5/2005 | Gerlach et al. | |
| 2005/0149026 A1 | 7/2005 | Butler et al. | |
| 2005/0165400 A1 | 7/2005 | Fernandez | |
| 2005/0192580 A1 | 9/2005 | Dalton | |
| 2005/0234457 A1 | 10/2005 | James et al. | |
| 2005/0261688 A1 | 11/2005 | Grady, Jr. et al. | |
| 2005/0277937 A1 | 12/2005 | Leung et al. | |
| 2005/0283154 A1 | 12/2005 | Orbay et al. | |
| 2006/0004361 A1 | 1/2006 | Hayeck et al. | |
| 2006/0009771 A1 | 1/2006 | Orbay et al. | |
| 2006/0095040 A1 | 5/2006 | Schlienger et al. | |
| 2006/0116678 A1 | 6/2006 | Impellizzeri | |
| 2006/0122602 A1 | 6/2006 | Konieczynski et al. | |
| 2006/0129148 A1 | 6/2006 | Simmons et al. | |
| 2006/0129151 A1 | 6/2006 | Allen et al. | |
| 2006/0149265 A1 | 7/2006 | James et al. | |
| 2006/0165400 A1 | 7/2006 | Spencer | |
| 2006/0167464 A1 | 7/2006 | Allen et al. | |
| 2006/0200147 A1 | 9/2006 | Ensign et al. | |
| 2006/0235400 A1 | 10/2006 | Schneider | |
| 2006/0235410 A1 | 10/2006 | Ralph et al. | |
| 2006/0259039 A1 | 11/2006 | Pitkanen et al. | |
| 2007/0010817 A1 | 1/2007 | de Coninck | |
| 2007/0043366 A1 | 2/2007 | Pfefferle et al. | |
| 2007/0093836 A1 * | 4/2007 | Derouet | 606/69 |
| 2007/0161995 A1 | 7/2007 | Trautwein et al. | |
| 2007/0162016 A1 | 7/2007 | Matityahu | |
| 2007/0162020 A1 | 7/2007 | Gerlach et al. | |
| 2007/0185488 A1 | 8/2007 | Pohjonen et al. | |
| 2007/0213828 A1 | 9/2007 | Trieu et al. | |
| 2007/0233106 A1 | 10/2007 | Horan et al. | |
| 2007/0260244 A1 | 11/2007 | Wolter | |
| 2007/0270691 A1 | 11/2007 | Bailey et al. | |
| 2007/0270832 A1 | 11/2007 | Moore | |
| 2007/0270833 A1 | 11/2007 | Bonutti et al. | |
| 2007/0276383 A1 | 11/2007 | Rayhack | |
| 2008/0021474 A1 | 1/2008 | Bonutti et al. | |
| 2008/0039845 A1 | 2/2008 | Bonutti et al. | |
| 2008/0086129 A1 | 4/2008 | Lindemann et al. | |

| | | | |
|---|---|---|---|
| 2008/0140130 A1 | 6/2008 | Chan et al. | |
| 2008/0154367 A1 | 6/2008 | Justis et al. | |
| 2008/0154368 A1 | 6/2008 | Justis et al. | |
| 2008/0154373 A1 | 6/2008 | Protopsaltis et al. | |
| 2008/0167717 A9 | 7/2008 | Trieu et al. | |
| 2008/0208259 A1 | 8/2008 | Gilbert et al. | |
| 2008/0300637 A1 | 12/2008 | Austin et al. | |
| 2009/0024161 A1 | 1/2009 | Bonutti et al. | |
| 2009/0076553 A1 | 3/2009 | Wolter | |
| 2009/0088807 A1 | 4/2009 | Castaneda et al. | |
| 2009/0143824 A1 | 6/2009 | Austin et al. | |
| 2009/0149888 A1 | 6/2009 | Abdelgany | |
| 2009/0192549 A1 | 7/2009 | Sanders et al. | |

FOREIGN PATENT DOCUMENTS

| | | | |
|---|---|---|---|
| CA | 2 047 521 | | 1/1992 |
| CA | 2 408 327 | | 3/2001 |
| CA | 2 536 960 A1 | | 3/2005 |
| CA | 2536960 | * | 3/2005 ................ 606/280 |
| CH | 611 147 A5 | | 5/1979 |
| CN | 1331572 | | 1/2002 |
| CN | 1373646 | | 10/2002 |
| CN | 1380043 | | 11/2002 |
| CN | 1188086 | | 2/2005 |
| CN | 101022767 | | 8/2007 |
| DE | 2 602 900 B | | 8/1978 |
| DE | 3 513 600 | | 10/1986 |
| DE | 3 804 749 | | 3/1989 |
| DE | 3 832 343 | | 3/1990 |
| DE | 9 000 161 U | | 4/1990 |
| DE | 323214 | | 1/1992 |
| DE | 4 341 980 B4 | | 6/1995 |
| DE | 4 343 117 A1 | | 6/1995 |
| DE | 4 438 261 C1 | | 9/1995 |
| DE | 4 438 264 A1 | | 3/1996 |
| DE | 19629011 A1 | | 1/1998 |
| DE | 198 58 889 A1 | | 6/2000 |
| DE | 199 62 317 A1 | | 3/2001 |
| DE | 102004035 546 | | 2/2006 |
| EP | 0 201 024 | | 11/1986 |
| EP | 0 207 884 A2 | | 1/1987 |
| EP | 0 274 713 A1 | | 7/1988 |
| EP | 0 355 035 B1 | | 2/1990 |
| EP | 0 486 762 | | 5/1992 |
| EP | 0 530 585 | | 3/1993 |
| EP | 0 705 572 | | 4/1996 |
| EP | 0 468 192 B1 | | 9/1996 |
| EP | 0799124 | | 10/1997 |
| EP | 0 828 459 B1 | | 3/1998 |
| EP | 0 760 632 B1 | | 9/2000 |
| EP | 1093385 | | 4/2001 |
| EP | 1 143 867 | | 10/2001 |
| EP | 1 169 971 | | 1/2002 |
| EP | 1 211 992 B | | 6/2002 |
| EP | 1330209 | | 7/2003 |
| EP | 1 364 623 B1 | | 11/2003 |
| EP | 1368073 | | 12/2003 |
| EP | 1 404 492 A1 | | 4/2004 |
| EP | 1 211 994 | | 4/2005 |
| EP | 1 211 993 | | 10/2005 |
| EP | 1 776 055 A1 | | 1/2006 |
| EP | 1 649 819 A1 | | 4/2006 |
| EP | 1 658 015 | | 5/2006 |
| EP | 1711114 | | 10/2006 |
| EP | 1718229 | | 11/2006 |
| EP | 1764054 | | 3/2007 |
| EP | 1813292 | | 8/2007 |
| EP | 1857073 | | 11/2007 |
| EP | 1931268 | | 6/2008 |
| EP | 1988837 | | 11/2008 |
| EP | 2019639 | | 2/2009 |
| FR | 2 233 973 | | 1/1975 |
| FR | 2 254 298 A1 | | 7/1975 |
| FR | 2 405 062 | | 5/1979 |
| FR | 2 405 705 | | 5/1979 |
| FR | 2 405 706 | | 5/1979 |
| FR | 2 496 429 | | 6/1982 |
| FR | 2 501 033 B | | 10/1985 |
| FR | 2 501 032 B | | 2/1987 |
| FR | 2 667 913 | | 4/1992 |
| FR | 2 698 261 | | 11/1992 |
| FR | 2 706 763 | | 12/1994 |
| FR | 2 739 151 | | 3/1997 |
| FR | 2 757 370 B | | 2/1999 |
| FR | 2 802 082 A1 | | 6/2001 |
| FR | 2 831 792 | | 5/2003 |
| FR | 2890848 | | 3/2007 |
| GB | 580571 | | 9/2006 |
| JP | 2003509107 | | 3/2003 |
| RU | 2 234 878 C2 | | 7/2001 |
| SU | 1279626 A1 | | 12/1986 |
| TW | 477687 | | 3/2002 |
| WO | WO 8904150 | | 5/1989 |
| WO | WO 9007304 | | 7/1990 |
| WO | WO 9609014 | | 3/1996 |
| WO | WO 9619336 | | 6/1996 |
| WO | WO 9709000 | | 6/1996 |
| WO | WO 9625892 | | 8/1996 |
| WO | WO 9629948 | | 10/1996 |
| WO | WO 9834553 | | 8/1998 |
| WO | WO 9834556 | | 8/1998 |
| WO | WO 9905968 | | 2/1999 |
| WO | WO 9925266 | | 5/1999 |
| WO | WO 9961081 | | 12/1999 |
| WO | WO 0018309 | | 4/2000 |
| WO | WO 0019264 | | 4/2000 |
| WO | WO 0036984 | | 6/2000 |
| WO | WO 0053110 | | 9/2000 |
| WO | WO 0053111 | | 9/2000 |
| WO | WO 0119264 | | 3/2001 |
| WO | WO 0119267 | | 3/2001 |
| WO | WO 0119268 | | 3/2001 |
| WO | WO 0178615 | | 10/2001 |
| WO | WO 0191660 | | 12/2001 |
| WO | WO 0200127 | | 1/2002 |
| WO | WO 0234159 | | 5/2002 |
| WO | WO 02058574 | | 8/2002 |
| WO | WO 02068009 | | 9/2002 |
| WO | WO 02096309 | | 12/2002 |
| WO | WO 03006210 | | 1/2003 |
| WO | WO 03106110 | | 12/2003 |
| WO | WO 2004032726 | | 4/2004 |
| WO | WO 2004032751 | | 4/2004 |
| WO | WO 2004086990 | | 10/2004 |
| WO | WO 2005018471 | | 3/2005 |
| WO | WO 2005018472 | | 3/2005 |
| WO | WO 2005032386 | | 4/2005 |
| WO | WO 2005062902 | | 7/2005 |
| WO | WO 2005079685 | | 9/2005 |
| WO | WO 2006007965 | | 1/2006 |
| WO | WO 2006039636 | | 4/2006 |
| WO | WO 2006068775 | | 6/2006 |
| WO | WO 2007014192 | | 2/2007 |
| WO | WO 2007014279 | | 2/2007 |
| WO | WO 2007025520 | | 3/2007 |
| WO | WO 2007041686 | | 4/2007 |
| WO | WO 2007092869 | | 8/2007 |
| WO | WO 2007130840 | | 11/2007 |
| WO | WO 2008022136 | | 2/2008 |
| WO | WO 2008033742 | | 3/2008 |
| WO | WO 2008064211 | | 5/2008 |
| WO | WO 2008077137 | | 6/2008 |
| WO | WO 2008079846 | | 7/2008 |
| WO | WO 2008079864 | | 7/2008 |
| WO | WO 2008116203 | | 9/2008 |
| WO | WO 2009029908 | | 3/2009 |

OTHER PUBLICATIONS

Smith & Nephew Brochure entitled 'PERI-LOC VLP Variable-Angle Locked Plating System Distal Tibia Locking Plates,' 04 pages (Oct. 2007).

Smith & Nephew Brochure entitled 'PERI-LOC VLP Variable-Angle Locked Plating System Distal Fibula Locking Plates,' 04 pages (Oct. 2007).

Smith & Nephew Brochure entitled 'PERI-LOC VLP Variable-Angle Locked Plating System Proximal Tibia Locking Plates,' 04 pages (Oct. 2007).

Smith & Nephew Brochure entitled 'PERI-LOC VLP Variable-Angle Locked Plating System Proximal Tibia Variable-Angle Locking Plates,' 04 pages (Nov. 2007).

Smith & Nephew Brochure entitled 'PERI-LOC VLP Variable-Angle Locked Plating System Improved Torsional Fatigue Properties with Thin Locked Versus Non-Locked Plate Constructs for Fixation of Simulated Osteoporotic Distal Fibula Fractures,' 04 pages (Nov. 2007).

Winkelstabilitat, litos Unidirectional locking screw technology, Jan. 15, 2008, 5 pages http://www.litos.com/pages/winkelstabilitaet_e.html.

"SMARTLock Locking Screw Technology," http://www.stryker.com/microimplants/products/cmf_smartlock.phn, Mar. 14, 2004.

International Search Report for PCT/US2006/028778, dated Apr. 19, 2007.

"Fracture and Dislocation Compendium," Orthopaedic Trauma Association Committee for Coding and Classification, Journal of Orthopaedic Trauma, vol. 10, Suppl., pp. v = ix, 1996.

English Abstract of JP 2002532185, Published Oct. 2, 2002.

English Abstract of ZA 200200992, Published Dec. 18, 2002, Applicant: SYNTHES AG.

DePuy Orthopaedics, Inc., entitled, 'Surgical Technique Distal Femoral Locked Plating System,' a Johnson & Johnson company, Polyax Wide Angle Freedom (2005).

NCB® Proximal Humerus Plating System, Surgical Technique, Zimmer, Inc., 2005.

Zimmer® NCB® Plating System, Zimmer, Inc., 2006.

NCB® Distal Femoral Plating System, Surgical Technique, Zimmer, Inc., 2005.

New Trauma Products from AO Development, News—No. 1, 2007.

Examiner's First Report on Australian Application No. 2006272646, mailed Mar. 21, 2011, 4 pages.

Examination Report for corresponding Japanese Application No. 2008-524048, mailed Oct. 25, 2011.

* cited by examiner

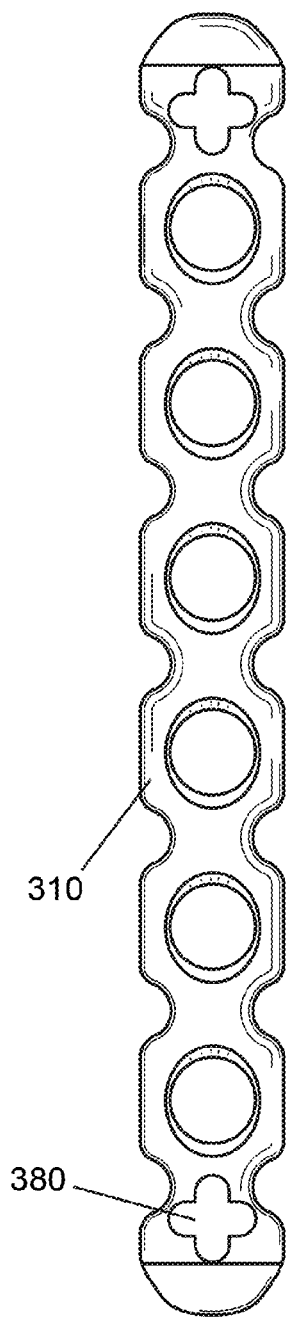
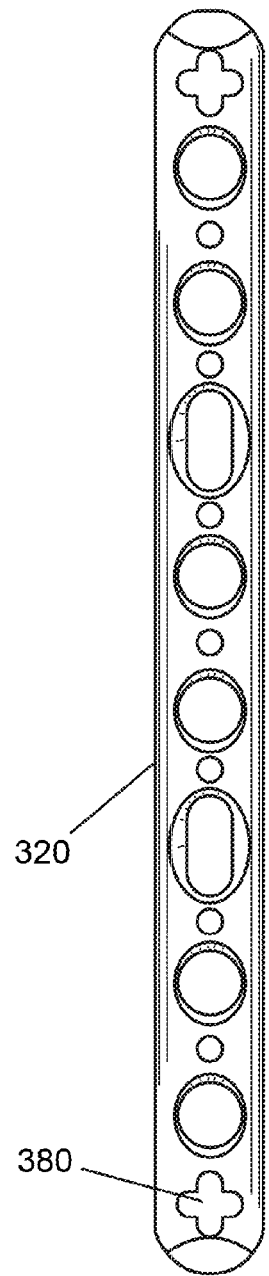
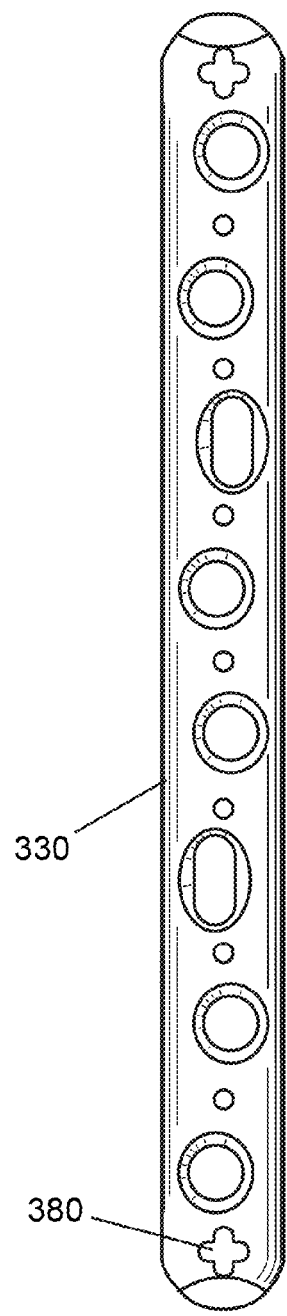
FIG. 44
FIG. 45
FIG. 46

BONE PLATE AND BONE PLATE ASSEMBLIES INCLUDING POLYAXIAL FASTENERS

CROSS REFERENCE TO RELATED APPLICATIONS

This application is a continuation-in-part of U.S. Application Ser. No. 11/996,795 filed Jan. 25, 2008 and entitled "Polyaxial Plate," which is a national phase application of PCT Application Serial No. PCT/US2006/028778 filed Jul. 25, 2006 and entitled "Systems and Methods for Using Polyaxial Plates," which claims the benefit of U.S. Provisional Application Ser. No. 60/702,231, filed Jul. 25, 2005 and entitled "Locking Screw," and this application is also a continuation-in-part of U.S. application Ser. No. 11/644,306, filed Dec. 22, 2006 and entitled "Bone Plates and Bone Plate Assemblies," now U.S. Pat. No. 7,905,910, which is a continuation of U.S. application Ser. No. 10/673,833, filed Sep. 29, 2003 and entitled "Bone Plates and Bone Plate Assemblies," now U.S. Pat. No. 7,179,260, the entire contents of prior applications are hereby incorporated by reference.

FIELD OF THE INVENTION

The present invention relates generally to orthopedic fixation devices and bone plating systems for fracture fixation, and particularly to systems and methods for using polyaxial fasteners within bone plating systems.

BACKGROUND OF THE INVENTION

Bone fractures are often repaired by securing a bone plate across the fracture. Depending upon which bone is to be treated, the bone plate may be straight or curved to match the contour of the bone for which it is designed. Bone plates may also be provided in many shapes and sizes. In cases where a bone is severely comminuted or if bone segments are missing, the use of bone plate and screw systems promotes healing of the fracture by providing a rigid fixation or support structure between the bone and the plate.

Bone plates may be secured to the bone in a number of ways. An existing solution is a plate and screw system where screws, called locking screws, are locked in the plate. First, a locking screw is threaded through an opening in the plate and into the bone. Then the locking screw is secured to the bone plate via threads on the head of the locking screw that cooperate with threaded openings in the bone plate. This secures the plate with respect to the bone and provides rigid fixation because the relationship between the plate and locking screw(s) is fixed. Because the threads on the head of the locking screw interdigitate with the threads in the plate opening, the plate and screws(s) form one stable system, and the stability of the fracture can be dependent upon the stiffness of the construct. Locking a screw into the plate can achieve angular and axial stability and eliminate the possibility for the screw to toggle, slide, or be dislodged, reducing the risk of postoperative loss of reduction.

However, although locking screws may reduce the incidence of loosening, they have limitations. Locking screws provide only one fixed angle relationship between the plate and the screw(s). They have a limited insertion angle because the threads of the head mate with the threads of the hole in one way only. The longitudinal axis of the screw aligns with the central axis of the hole, and no angular variation is allowed. In short, locking screws are unidirectional, limiting their use in some instances. For example, when treating a severe fracture, bone fragments may be shattered and in irregular positions. Although a surgeon may wish to obtain the benefits of a locking screw and bone plate used together, the pre-determined angle at which the locking screw extends from the plate may not be the angle that would allow the surgeon to "grab" (or seize, or otherwise secure) the desired, random bone fragment. Rather, screws with more angular flexibility (such as compression screws) may be required. Moreover, locking screws secured in a plate have a limited capability to compress bone fragments, since once the screw is fully rotated to lock with the plate, it can rotate no further to compress the plate to the bone. Conversely, there may be situations where the screw rotates sufficiently to capture bone, but does not rotate sufficiently to lock to the plate.

In short, while locking screws were useful to provide rigid fixation, they often could not perform other functions typically performed by traditional non-locking or compression screws (also referred to as cortical or cancellous screws). Although non-locking screws are secured into bone in the same way that locking screws are, they are not secured to the plate. Their heads are typically rounded where they contact the bone plate and they do not have threads that lock into the plate. Thus, while not optimal in providing a rigid construct between the screw and plate, they can be inserted at various angles because they are not limited by the thread-to-thread contact of locking screws with the bone plate.

Given the unique contributions of each of locking and non-locking screws, bone plating systems were developed that provided surgeons the option of using both types of screws in an installation. In this way, surgeons could choose intra-operatively whether to use the bone plate with compression screws, locking screws, or a combination of both and thus more effectively tailor the installation to the particular situation.

In some embodiments, these systems provide plates with some threaded holes (that may receive either locking screws or non-locking screws) and some non-threaded holes (for non-locking screws). Some systems provide partially threaded slots to allow either non-locking or locking screws to be used together. Such combination slots provide surgeons with the intra-operative choice about whether to use the plate with locking screws, non-locking screws, or a combination of both. These combination slots typically have a partially threaded opening that can receive either a compression screw or a locking screw. However, because these combination slots are only partially threaded, the locking screw(s) may not be able to maintain the fixed angular relationship between the screw(s) and plate under physiological loads. Specifically, the locking screws within the plate are only partially captured and thus only partially surrounded by threads. Under high stress and loading conditions, the slot may distort and allow the fixed angular relationship between the locking screw and plate to change. This can result in loss of fixation or loss of established intra-operative plate orientation. Moreover, the locking screw can still only be inserted at a single angle—the predetermined angle defined by the manufacturer.

Additionally, current bone plate and screw systems still limit a surgeon's ability to both (a) lock a fastener with respect to the bone plate, but still (b) allow the fastener to extend from the bone plate at various angles. Locking screws lock into the plate, but only in a single angular configuration, and non-locking screws allow various angle configurations, but they do not provide a stable construct with the plate. Accordingly, none of these options allow a surgeon to capture bone fragments that do not fall in line with the axis of the opening provided on the plate in a rigid fashion. Thus, currently available options can still lead to mal-alignment and poor clinical results.

There have been some attempts to provide polyaxial locking systems. For example, one effort includes providing holes that accept fixed angle locking pegs and multidirectional locking pegs, with a threaded cap inserted over the multidirectional peg to hold it in place. Such a system can be cumbersome to use because, although the multidirectional peg can be inserted at any angle, the surgeon then needs to thread a small cap onto the top of the peg head and into the plate, requiring an extra step, extra time, and extra instrumentation. Such systems also fail to allow the use of non-locking members in conjunction with the locking and multidirectional pegs.

Other systems that have attempted to offer polyaxial fixation include providing a bone plate with deformable inserts at the hole peripheries made out of a deformable material, with the remaining part of the plate made of titanium. The plate is manufactured and the deformable inserts are then pushed into the hole peripheries and engaged in place by deformation and pressure. When screws are inserted, the deformable inserts deform and are compressed between the screws and the edges of the holes of the plate, which holds the screws and inserts in place. There are challenges with such systems, however. First, the deformable inserts cannot be used with non-locking screws. Second, the deformable inserts do not have the strength to receive and hold a regular locking screw. Thus, the unavailability of non-locking screws and regular locking screws do not provide the surgeon with options. Finally, plates with deformable inserts are more expensive to manufacture than regular bone plates.

Accordingly, there exists a need for an improved bone plating system that overcomes the deficiencies of the prior art. There is a need for a system that provides a stable connection between a bone and a bone plate using a fastener that permits different angles to be obtained between the bone plate and the fastener, while the fastener also locks into the bone plate. This would allow surgeons to capture random bone fragments that are in irregular positions, for example, in cases of severe fractures with highly fragmented bone fragments. In these and other cases, it would be advantageous to provide a fastener and plate system that allows the surgeon to choose the angle at which the screw is inserted through, and rigidly affixed in, an opening of the plate.

Such an improvement would allow a surgeon to direct the fastener toward bone fragments that are not necessarily located directly beneath the opening in the plate. It would also provide flexibility in the placement of the plate in relation to the bone fracture. Allowing surgeons to choose the angle at which the fastener is inserted into the plate would lead to better tailoring of the system to the specific nature of the bone fracture to be treated. It would also allow surgeons to adjust their strategy as necessary after the surgical site has been accessed, but prior to insertion of the fastener into bone material. Additionally, embodiments described herein provide for a more secure polyaxial insertion than what is available in known systems which contain a plate with a deformable insert.

BRIEF SUMMARY OF THE INVENTION

In certain embodiments there is a bone plate comprising a first opening. The first opening may be threaded, and the threads may be made of a first material. A first fastener may be inserted into the first opening in order to secure the bone plate to the bone. In certain embodiments the first fastener has a head at least partially made of a polymeric material that is softer than the first material of the threads of the first opening. In use, the first fastener is positioned and rotated in the first opening, and the threads of the first opening form "threads" into the polymeric material of the first fastener to thereby fix the orientation of the first fastener relative to the first opening. Thus, the first fastener may be secured at one of a plurality of possible angles within the first opening. This may help in capturing "renegade" or random bone fragments that have split from the bone during fracture, and may help in securing the bone fragments to the bone plate.

The first opening is configured to interchangeably accept other types of fasteners in addition to the first fastener. For example, there is provided a second fastener with a threaded head, wherein the threads on the head are configured and dimensioned to mate with the threads of the first opening (also called a locking fastener). In use, when the second fastener is inserted into the first opening, the threads of the first opening and the threads on the head of the second fastener engage, which "locks" the second fastener in place within the first opening.

The first opening may additionally accept a third fastener comprising a head with a substantially spherical and non-threaded portion (also called a non-locking fastener). In use, when the third fastener is inserted into the first opening, the spherical portion of the head contacts, but does not otherwise engage with, the threads of the first opening. Thus the third fastener can be inserted at various angles because it is not limited by the thread-to-thread contact with the first opening.

In certain embodiments the first opening may have a frustoconical-shaped top portion that helps push or pull the bone plate in a particular direction as a fastener is inserted into the first opening. In particular, the head of a fastener may come into contact with and ride along the frustoconical-shaped top portion of the first opening, thus moving the bone plate in a particular direction. In certain embodiments, additional openings may be provided on the bone plate, including other types of threaded openings, non-threaded openings, provisional fixation holes, K-wire holes, combination holes, finned openings, and slots. The different types of fasteners described above—including the first, second, and third fasteners described above—may be used as appropriate in the different types of openings.

BRIEF DESCRIPTION OF THE SEVERAL VIEWS OF THE DRAWINGS

FIGS. 33-50 are views of various exemplary bone plate configurations according to various embodiments of the present invention.

FIG. 51 shows a provisional fixation slot according to one embodiment of the present invention.

DETAILED DESCRIPTION OF THE INVENTION

Figure 1:
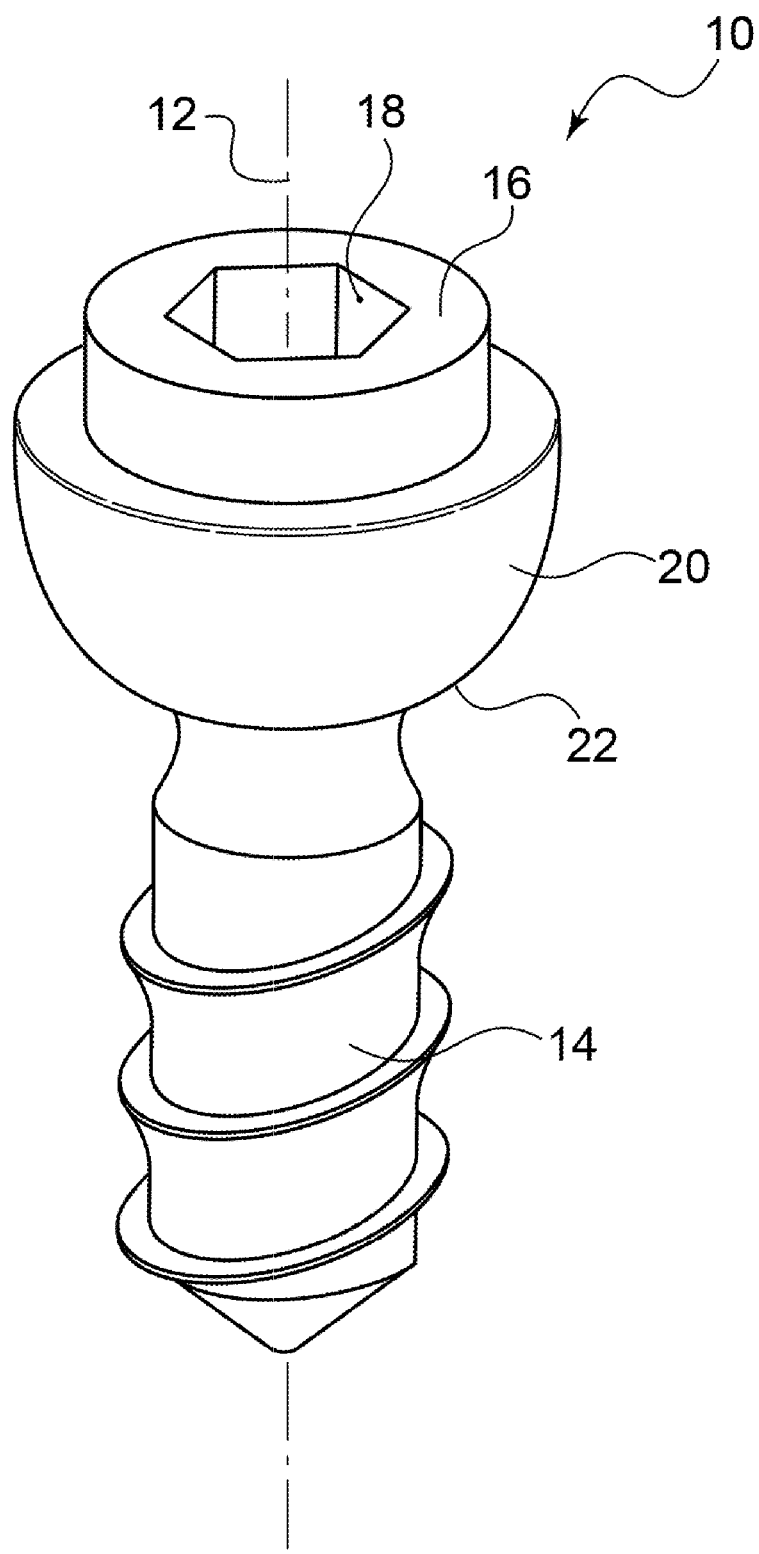
FIG. 1 shows perspective view of one embodiment of a fastener of this invention.
Figure 2:
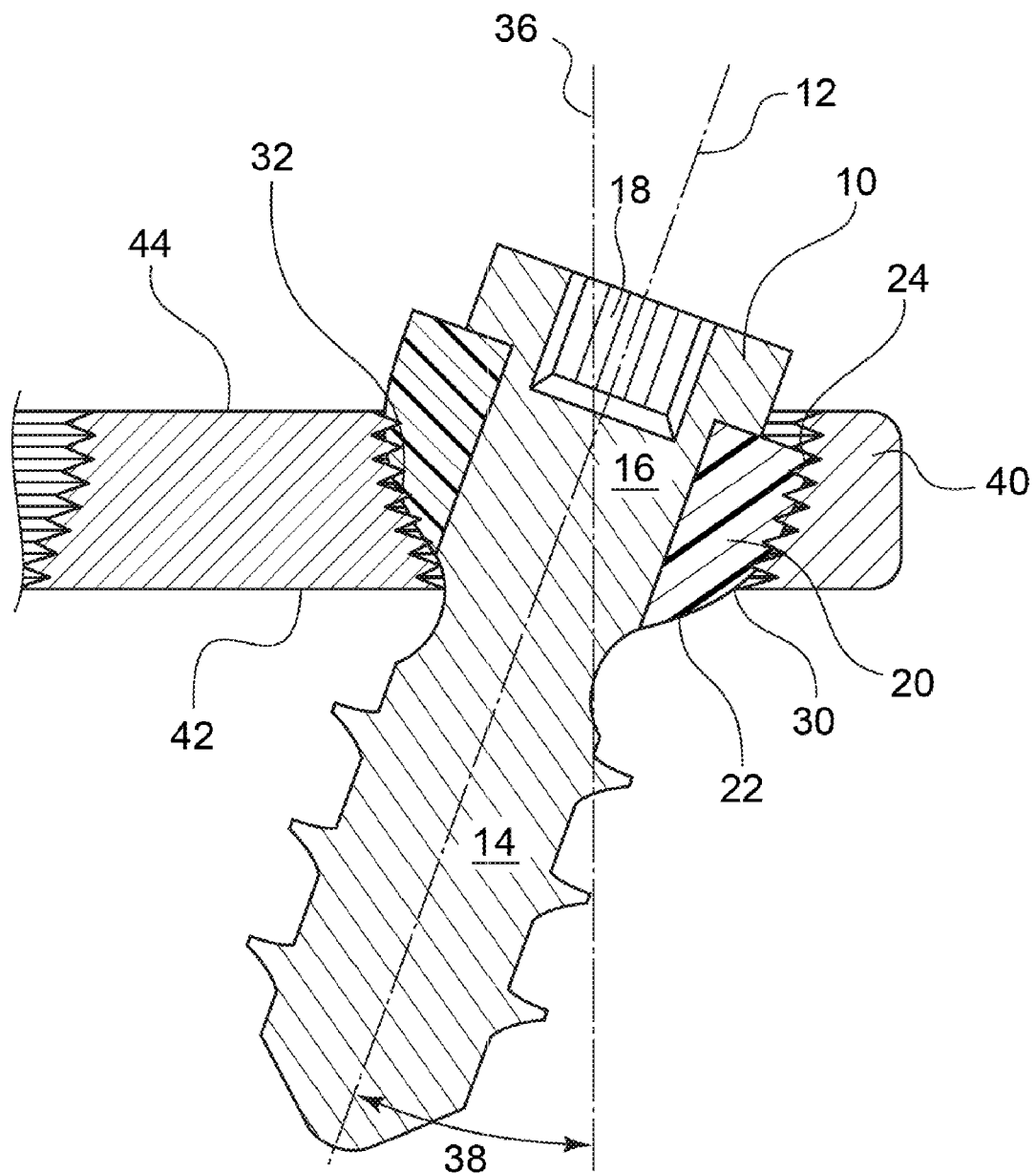
FIG. 2 shows a cross-sectional view of the fastener of FIG. 1 positioned in a bone plate.

Embodiments of the present invention provide a fastener 10 for polyaxial fixation in a variety of different types of bone plate openings. FIGS. 1 and 2 illustrate an embodiment of one such fastener. This application uses the terms "fastener" and "screw" interchangeably. Fastener 10 includes a head 16 and a shaft 14 that defines a fastener central axis 12. In FIGS. 1 and 2, the shaft 14 is threaded. The shaft 14 may be fully threaded, partially threaded, comprise a helical blade, and/or may comprise one or more tacks, deployable talons, expandable elements, or so forth. Any feature that allows shaft 14 to engage bone is considered within the scope of this invention and may be referred to generally as a "threaded shaft" for the sake of convenience. It is also possible that shaft 14 is not threaded, so that fastener 10 takes the form of a peg or a pin. This alternative embodiment may be preferred in certain procedures where, for instance, the main goal is to prevent tilting of a bone segment or in procedures where there is no concern of fastener 10 pulling out from the bone and hence no need for shaft 14 to be threaded or otherwise configured to engage bone. The end of shaft 14 may be a self-tapping or self-drilling tip.

The head 16 of the fastener 10 also includes a fastener seating surface 20. The fastener seating surface 20 may encompass the entire head 16 of the fastener 10, or it may only partially encompass the head 16. For example, in FIG. 1 the height of the fastener seating surface 20 is less than the height of the head 16, so that a portion of the head 16 protrudes above the fastener seating surface 20. In other embodiments, however, the fastener seating surface 20 encompasses the entire head 16 of the fastener 10. In some embodiments, at least portions of the fastener seating surface 20 are smooth and contoured, as shown in FIG. 1. The smooth portions 22 of the fastener seating surface 20 may be seen in FIGS. 1 and 2.

Fastener 10 will typically have a bore 18 for receiving a driver in order to drive fastener 10 into the bone plate and into bone. The bore 18 may be any size and shape, for example, it may have a hexagonal configuration to receive a corresponding hexagonal driver, a Phillips screw head, a flat-head, a star configuration, Torx, or any other appropriate configuration that can cooperate with a driver to place fastener.

FIG. 2 illustrates fastener 10 engaged in a bone plate 40 having an upper surface 44, a bone contacting surface 42, and a threaded opening 30 extending between the upper surface 44 and the bone contacting surface 42. The terms "opening" and "hole" are used interchangeably herein. More specifically, opening 30 of plate 40 is shown having opening threads 32 and an opening central axis 36. Opening threads 32 are typically any standard-type thread. For example, the opening threads 32 may be a continuous ridge or a non-continuous ridge. It may comprise a portion of a revolution, one complete revolution, multiple revolutions, a single lead, or multiple leads, or any other threads known in the art. Additionally or alternatively, opening threads 32 may include any other surface that will engage with and seat with features of the fastener 10. For example, opening threads 32 may have a series of dimples, ridges, bumps, textured areas, or any other surface that can secure with features of the fastener 10 as described herein. In short, any type of thread is intended for use with various embodiments of this invention.

The fastener seating surface 20 may be formed of any material but it is preferable that the fastener seating surface 20 be made of a material with a yield strength that is lower than that of the material defining the opening 30. In some embodiments the fastener seating surface 20 is made from polyethylene, for example.

In use, fastener 10 is positioned and rotated in opening 30. Rotating the fastener 10 with respect to the opening 30 causes deformation of the fastener seating surface 20 because the fastener seating surface 20 is made from a material that is weaker than that defining the opening 30. More specifically, the opening threads 32 tap "threads" into the head 16 of the fastener 10 (and more particularly the fastener seating surface 20) and thereby fixes the orientation of the fastener 10 relative to the opening 30. The resulting threaded portions 24 on the fastener seating surface 20 are shown in FIG. 2. As may be seen from FIG. 2, there may be smooth portions 22 where the opening threads 32 have not tapped into the fastener seating surface 20. Thus in some embodiments the entire head 16 of the fastener 10 may not be tapped. Additionally, the location of the smooth portions 22 and the threaded portions 24 will change depending upon the insertion angle 38 in which the fastener 10 is inserted.

Given that there are no pre-existing threads on the head of fastener 10, the fastener 10 may be inserted and locked into the opening 30 in any angular orientation. Embodiments of the invention provide for an insertion angle 38 between the fastener central axis 12 and the opening central axis 36. The insertion angle 38 may also be described as the direction along which fastener 10 is inserted through opening 30 and driven into bone material. In some embodiments the opening central axis 36 and the fastener central axis 12 are co-linear so that the insertion angle 38 is zero. But in other embodiments the opening central axis 36 and the fastener central axis 12 are not co-linear and the insertion angle 38 has some value. FIG. 2 has an insertion angle 38 that is approximately 20-30°; however, other insertion angles 38 are within the scope of the invention.

The fastener 10 may be positioned in the opening 30 and fixed in the plate 40 at various insertion angles 38. This may help in capturing "renegade" or random bone fragments that have split from the bone during fracture and in securing the bone fragments to the plate 40. For example, if a wrist bone is broken, there will be numerous fragments that may shatter in various directions. Fastener 10 may be inserted into plate 40 at various insertion angles 38 in order to capture the renegade fragments that would otherwise not be secured to a bone plate 40 using only a locking or a non-locking fastener.

Fastener 10 may be used in connection with any type of threaded hole (including, but not limited to, any threaded hole disclosed herein) on any type of bone plate. The bone plate may be adapted to contact one or more of a femur, a distal tibia, a proximal tibia, a proximal humerus, a distal humerus, a clavicle, a fibula, an ulna, a radius, bones of the foot, or bones of the hand. The bone plate may be curved, contoured, straight, or flat. It may be a periarticular plate or a straight plate. The plate may have a head portion that is contoured to conform to a particular bone surface, such as a metaphysis or diaphysis, that flares out from the shaft portion, that forms an L-shape, T-shape, Y-shape, with the shaft portion, or that forms any other appropriate shape to fit the bone to be treated (not shown in figures).

The bone plate may be formed of titanium, stainless steel, cobalt chrome, plastic—such as polyetheretherketone (PEEK), polyethylene, ultra high molecular weight polyethylene (UHMWPE), or a carbon composite—resorbable polylactic acid (PLA), polyglycolic acid (PGA), combinations or alloys of such materials or any other appropriate material that has sufficient strength to be secured to and hold bone, while also having sufficient biocompatibility to be implanted into a body. Although the above list of materials includes many typical materials out of which bone plates are made, it should be understood that bone plates comprised of any appropriate material are within the scope of this invention.

In some embodiments, openings 30 may be provided on a bone plate 40 in combination with a variety of other types of openings (e.g., other types of threaded openings, non-threaded openings, provisional fixation or K-wire holes, combination holes, etc.), including but not limited to those discussed in reference to FIGS. 3-51. It should be understood that these various types of openings may be used on any type of bone plates, in any combination and in any size.

Figure 3:
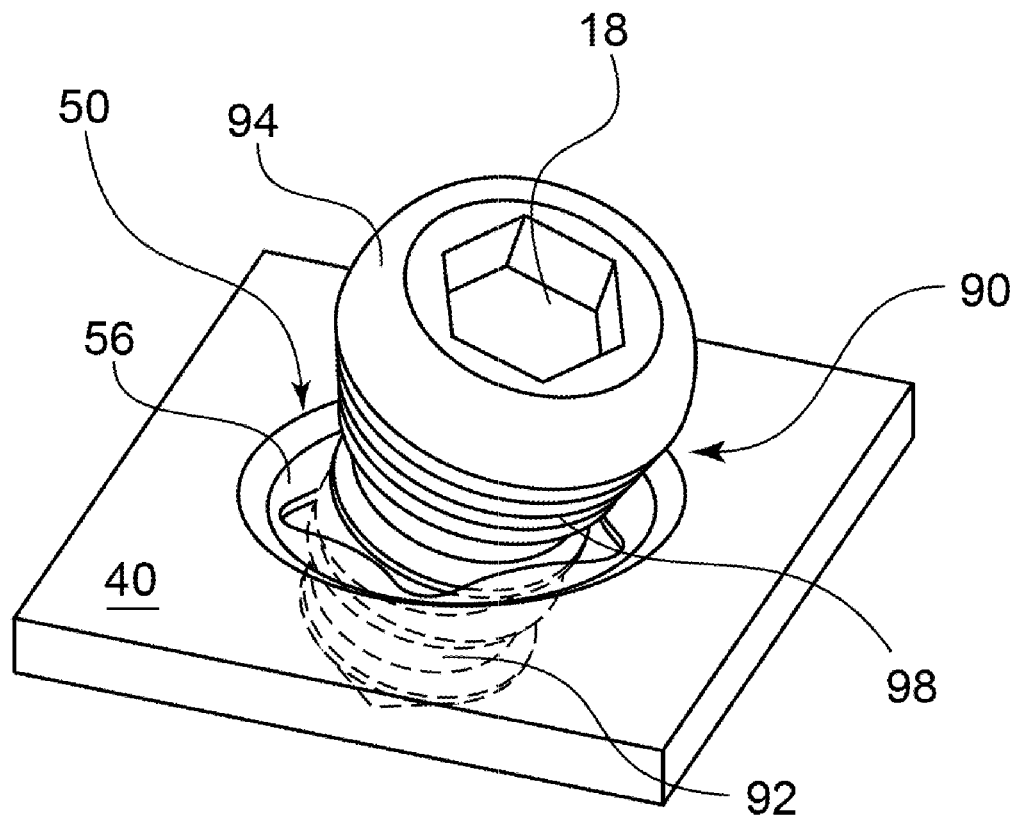
FIG. 3 shows a fragmentary top perspective view of a bone plate having fins according to one embodiment of the invention with a fastener inserted therein.
Figure 4:
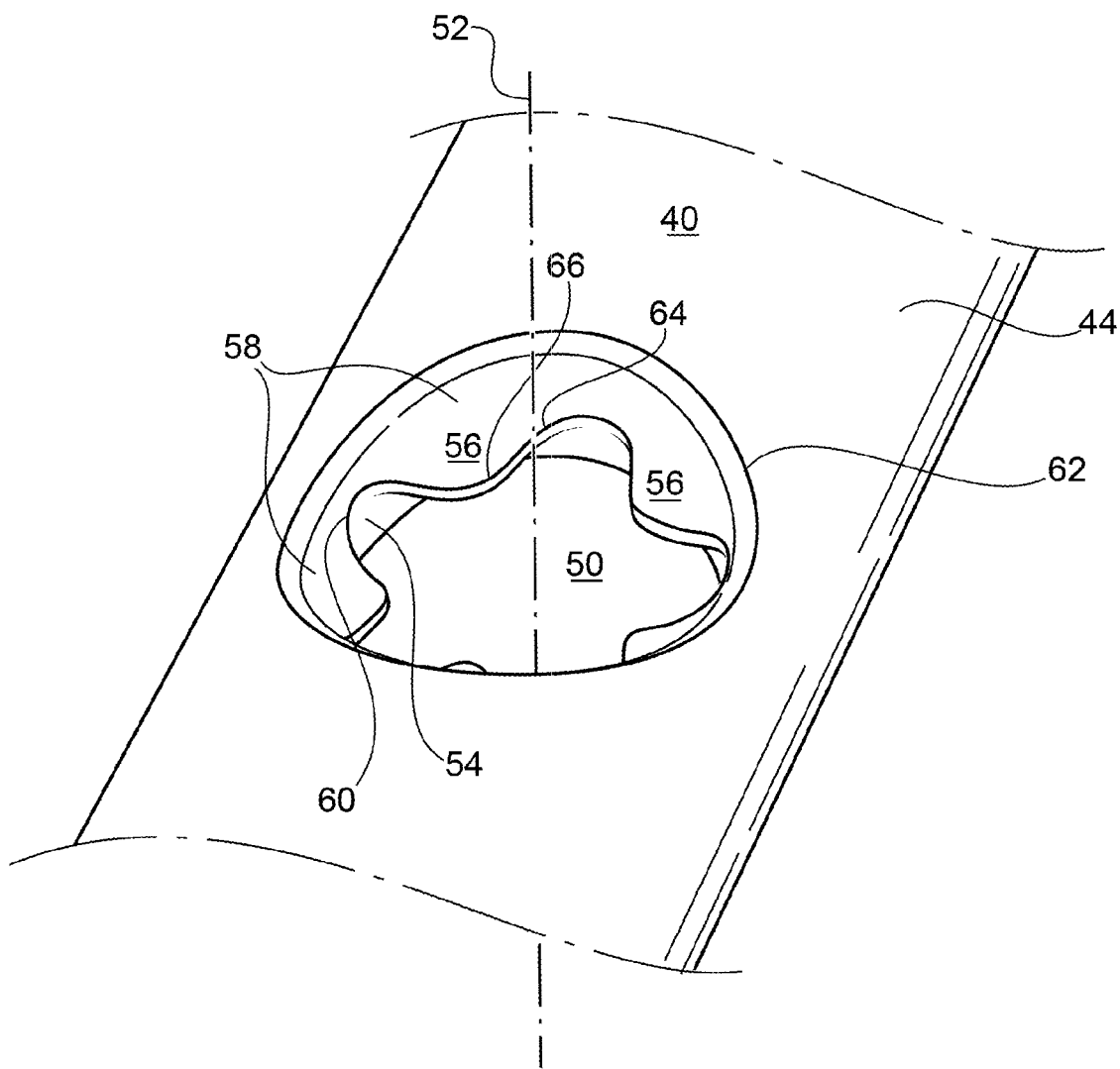
FIG. 4 shows a fragmentary top perspective view of the bone plate of FIG. 3.
Figure 8:
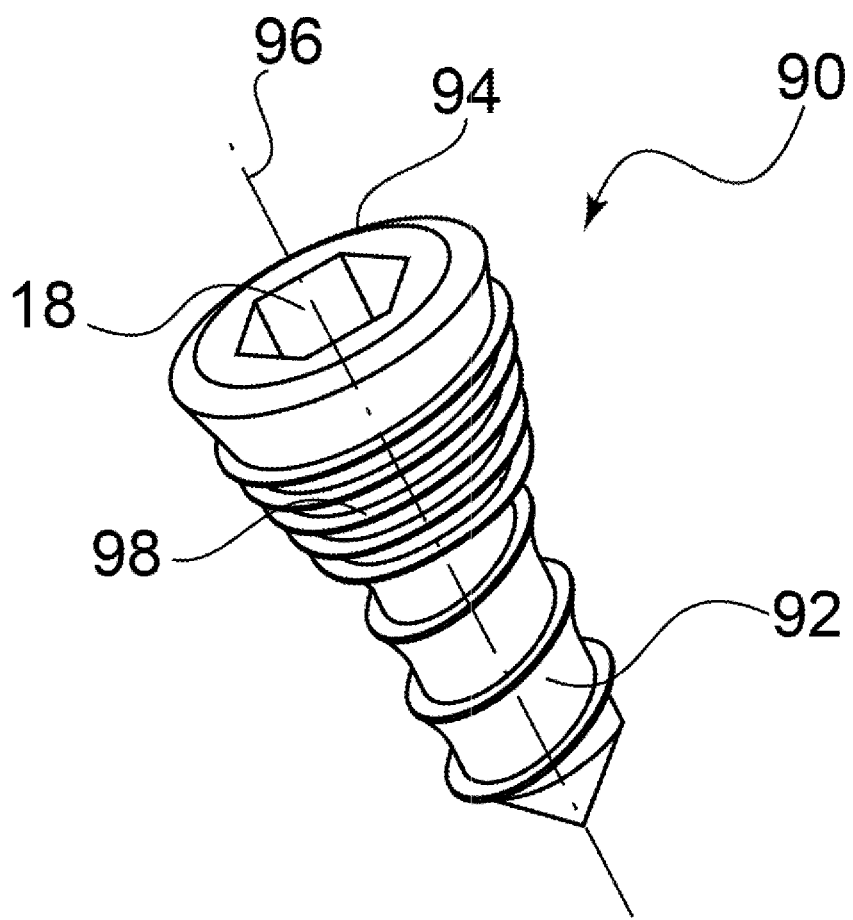
FIG. 8 shows a perspective view of one embodiment of a fastener for use with various bone plates described herein.
Figure 13:
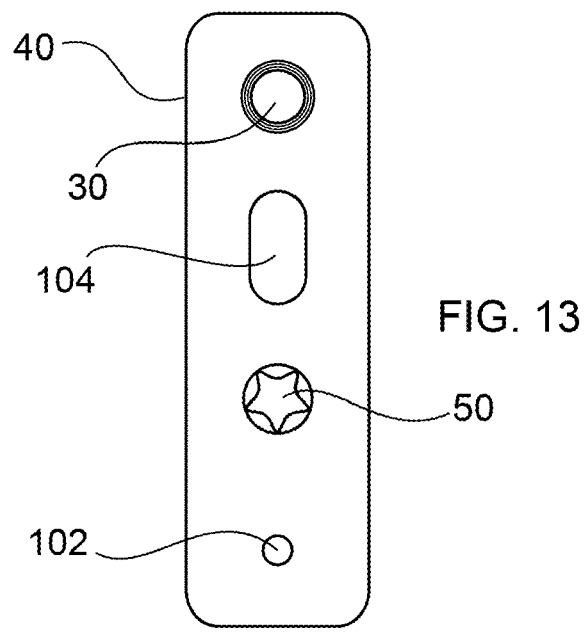
FIGS. 13-17 show alternative shapes and types of bone plates that may be used with various embodiments of this invention.
Figure 14:
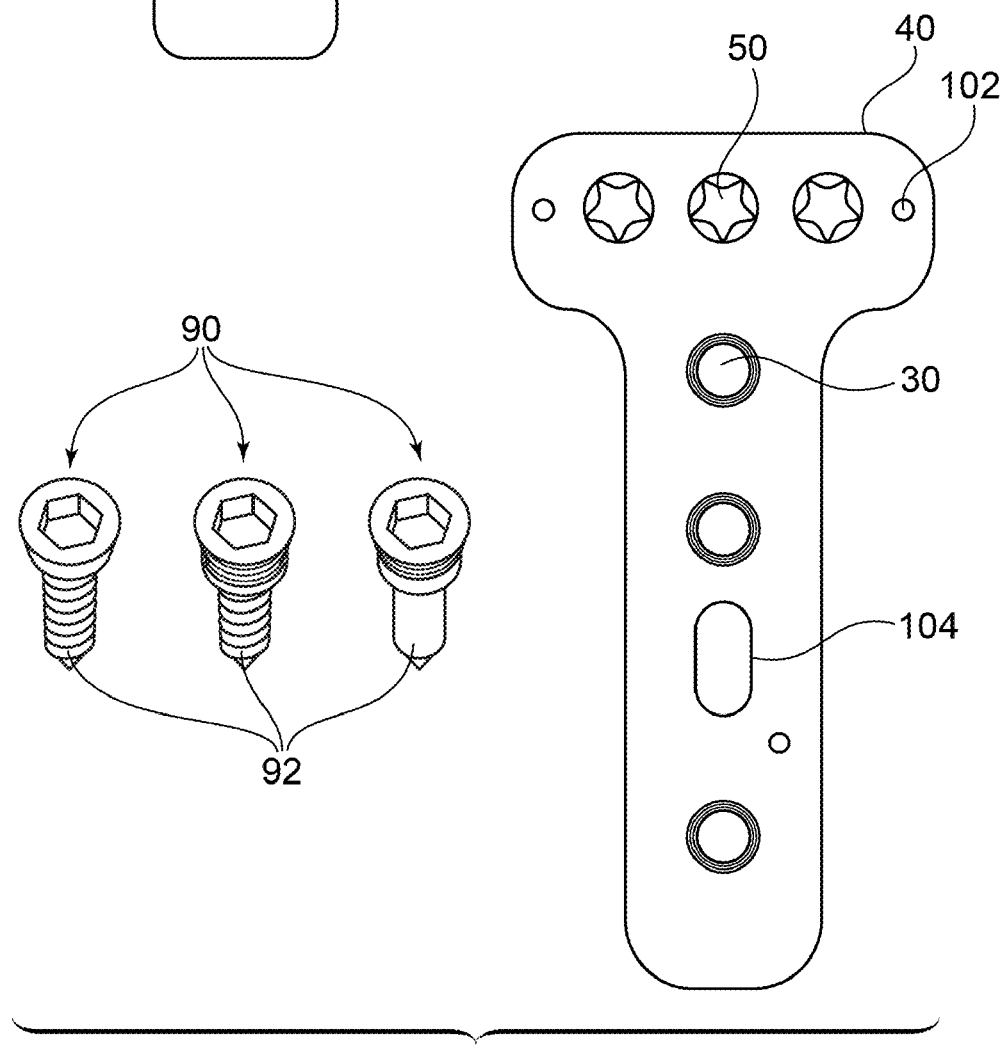
Figure 17:
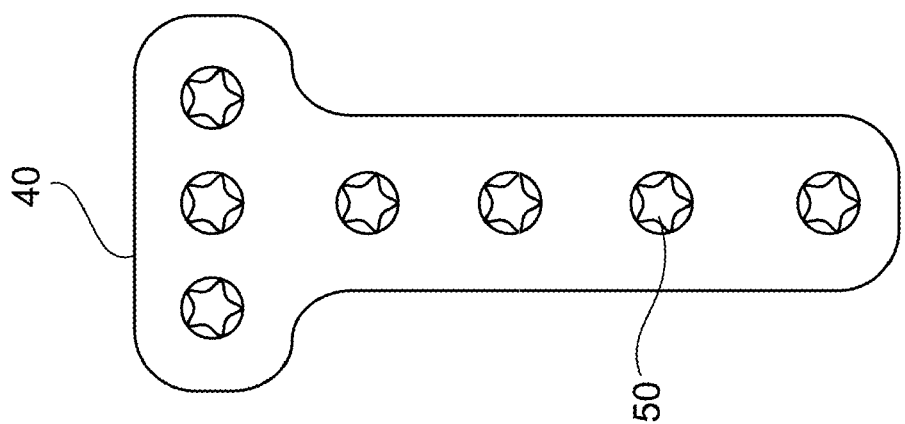
Figure 16:
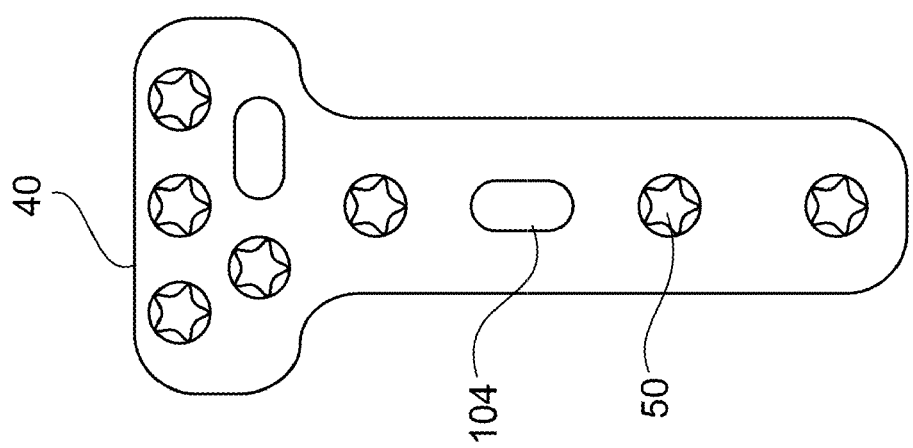
Figure 15:
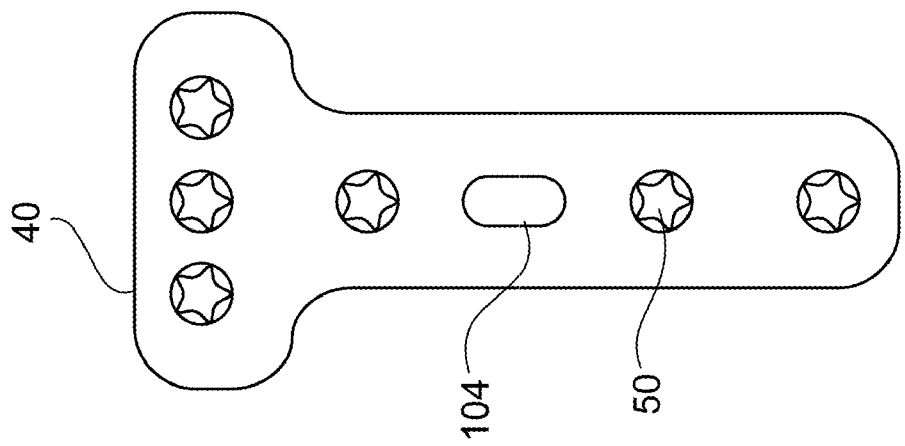

In one embodiment, such as shown in FIGS. 13 and 14, bone plate 40 includes openings 30 in combination with finned openings 50. Embodiments with finned openings 50 may be combined with a fastener 90. Fastener 90 may have a shaft 92 with a longitudinal axis 96. As shown in FIG. 14, the shaft 92 may be threaded or non-threaded. In certain embodiments as shown in FIGS. 3 and 8, the head 94 of fastener 90 has at least one set of threads 98. Threads 98 are typically any standard-type thread. For example, the threads 98 may be a continuous ridge or a non-continuous ridge. They may comprise a portion of a revolution, one complete revolution, multiple revolutions, a single lead, or multiple leads, or any other threads known in the art. Additionally or alternatively, head 94 of fastener 90 may include any other surface that will engage with and seat within specific features of plate 40 (described further below). For example, head 94 may have a series of dimples, ridges, bumps, textured areas, or any other surface that can secure fastener 90 as described herein. As will be described in more detail below, threads 98 of head 94 are adapted to engage, associate with, or otherwise cooperate with fins 56 of finned opening 50. In short, any type of threaded fastener head is intended for use with various embodiments of this invention.

Plate 40 of FIG. 13 has a finned opening 50 (shown in detail in FIG. 4) with an inner surface 54 from which a series of concavely indented, inwardly protruding fins 56 extend. Fins 56 extend into finned opening 50 toward central axis 52. The bases 58 of fins 56 form a concave portion 60 at or near a substantially round upper circumference 62 of upper surface 44. (The term "round" circumference is intended to refer to any round shape, such an a circle, an oval, an egg-shaped circumference, or any other opening shaped to receive the head 94 of a fastener 90.) The bases 58 of the fins 56 may all meet in substantially the same plane and then angle downwardly and inwardly at a similar angle or slope.

It bears noting that the concave portion 60 is smooth and non-threaded. In fact, there are not any threads on concave portion 60 or anywhere on inner surface 54 of finned opening 50. The lack of threads helps ease the manufacturing of plate 40, and allows plate 40 to be manufactured as thinly as desired.

The dimensions of fins 56 are typically dependent at least in part upon the pitch and threads of fastener 90. For example, a larger plate 40 for use with a larger fastener 90 (e.g., for use on a femur bone) will likely be thicker and will have larger and thicker fins 56 than a smaller plate 40 (e.g., for use on a smaller bone). In specific embodiments, the fins 56 are particularly thin so that they can be moved up or down and deformed upon pressure. In some embodiments, the fins 56 may be pressed toward the edges of the finned opening 50. A non-limiting exemplary range of thicknesses for fins 56 may be from about 0.5 mm to about 5 mm, although larger and smaller sizes are possible. In theory, the fins 56 are intended to fit between threads 98 on the thread form of fastener 90, as shown in FIG. 3.

Figure 7:
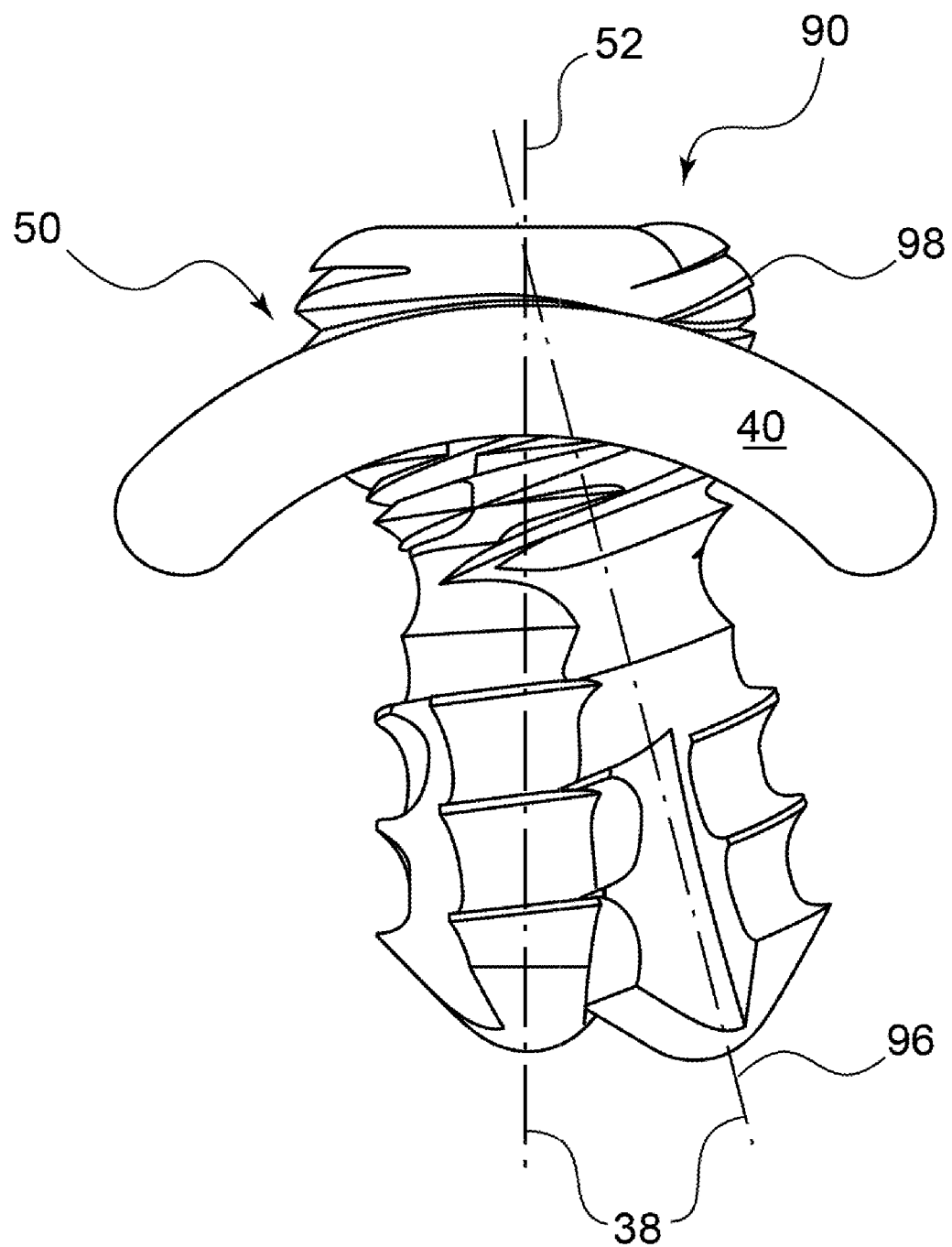
FIG. 7 shows a side elevational view of the bone plate of FIG. 5.

Providing a non-threaded inner surface 54 also allows the fastener 90 to be inserted into finned opening 50 at any desired insertion angle 38, as illustrated by FIG. 7. Embodiments of the invention provide for an insertion angle 38 between the longitudinal axis 96 of the fastener 90 and the central axis 52 of finned opening 50. The insertion angle 38 may also be described as the direction along which fastener 90 is inserted through finned opening 50 and driven into bone material. In some embodiments the central axis 52 and the longitudinal axis 96 are co-linear so that the insertion angle 38 is zero. But in other embodiments the central axis 52 and the longitudinal axis 96 are not co-linear and the insertion angle 38 has some value. FIG. 7 illustrates one fastener 90 having an insertion angle 38 of approximately 0° and another fastener 90 having an insertion angle 38 of approximately 20-30°; however, other insertion angles 38 are within the scope of the invention. Varying the insertion angle 38 is possible because there are not any threads in the finned opening 50 to interfere with the desired insertion angle 38. The fins 56 are intended to slightly bend or deform in order to secure the fastener 90 in place in finned opening 50. Fins 56 actually engage threads 98 or other surface of fastener 90.

Figure 10:
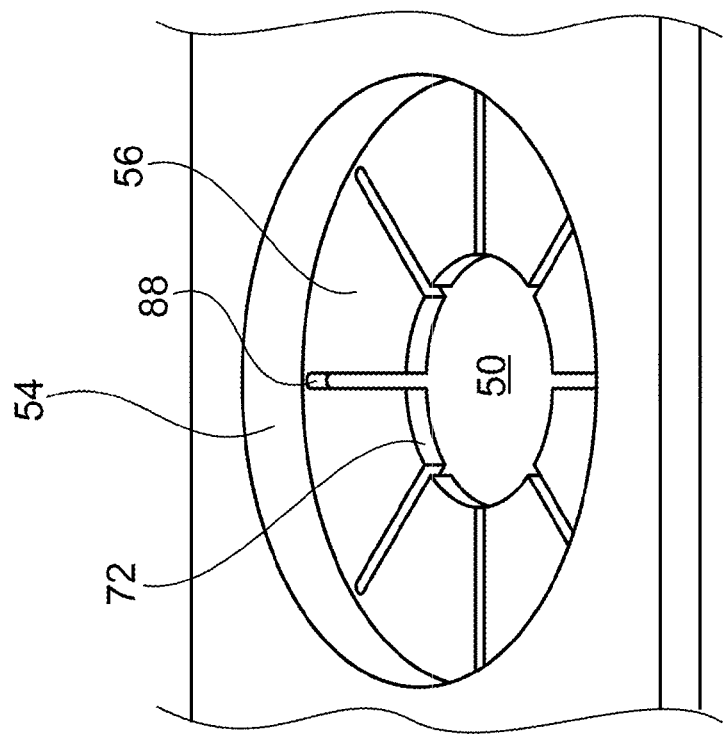
FIG. 10 shows a fragmentary perspective view of a bone plate with the opening of FIG. 9.
Figure 9:
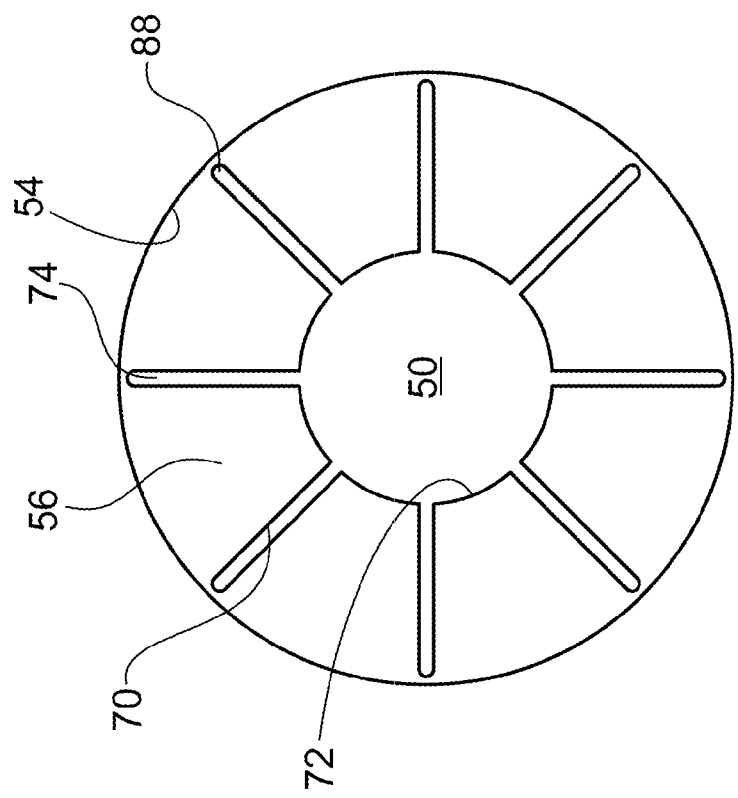
FIG. 9 shows a top plan view of an alternate embodiment of an opening for use in a bone plate.

Referring back to FIG. 4, in the embodiment shown, as fins 56 extend toward central axis 52, they taper to form tapered sides 64. The fins 56 end at rounded tips 66, although tips 66 can be pointed, square, rectangular, or any other appropriate configuration. For example, as shown in FIGS. 9 and 10, fins 56 may have straight edges or sides 70 and straight ends 72. This embodiment shows fins 56 that are partially rectangular-shaped. The openings 74 between fins 56 are slit-shaped.

Figure 12:
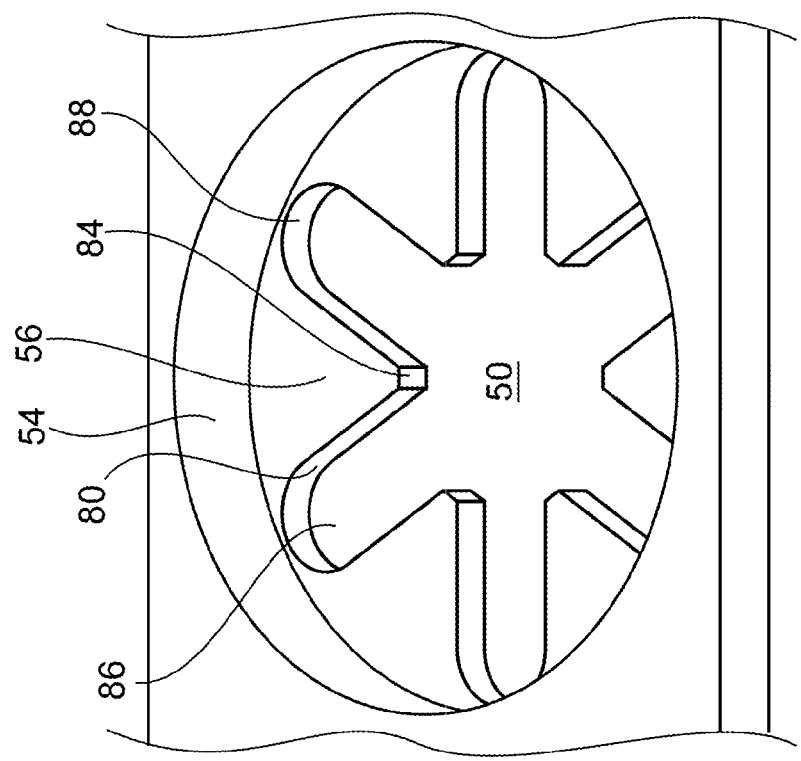
FIG. 12 shows a fragmentary top perspective view of a bone plate with the opening of FIG. 11.
Figure 11:
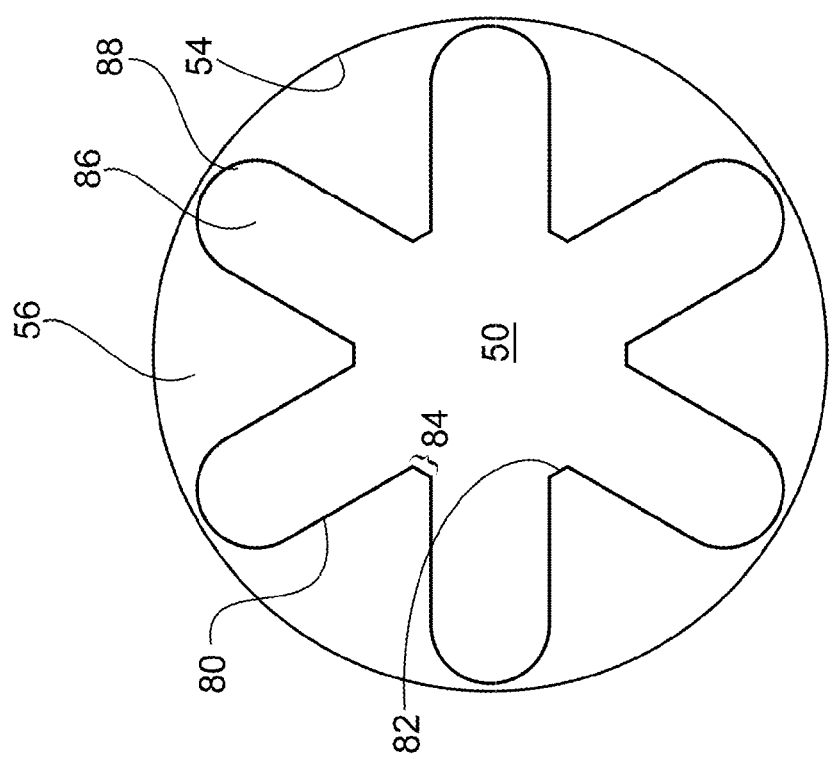
FIG. 11 shows a top plan view of a further embodiment of an opening for use in a bone plate.

An alternate embodiment is shown in FIGS. 11 and 12, which illustrate fins 56 with a more triangular shape. In this embodiment, fins 56 are shown having sides 80 that taper inwardly and end edges 82 that are flat and small, forming the apex area 84 where adjacent sides 80 converge. Openings 86 in FIG. 11 are wider than openings 74 in FIG. 9. Both sets of openings 86, 74 in these alternative embodiments are shown having rounded backs 88, where they meet inner surface 54 of finned opening 50. It should be understood however, that these are merely examples of fin 56 shapes and that any appropriate shapes are possible and considered within the scope of this invention. Non-limiting examples include trapezoidal, square, round, circular, triangular (with a pointed tip instead of apex area 84), and any other possible option.

Figure 6:
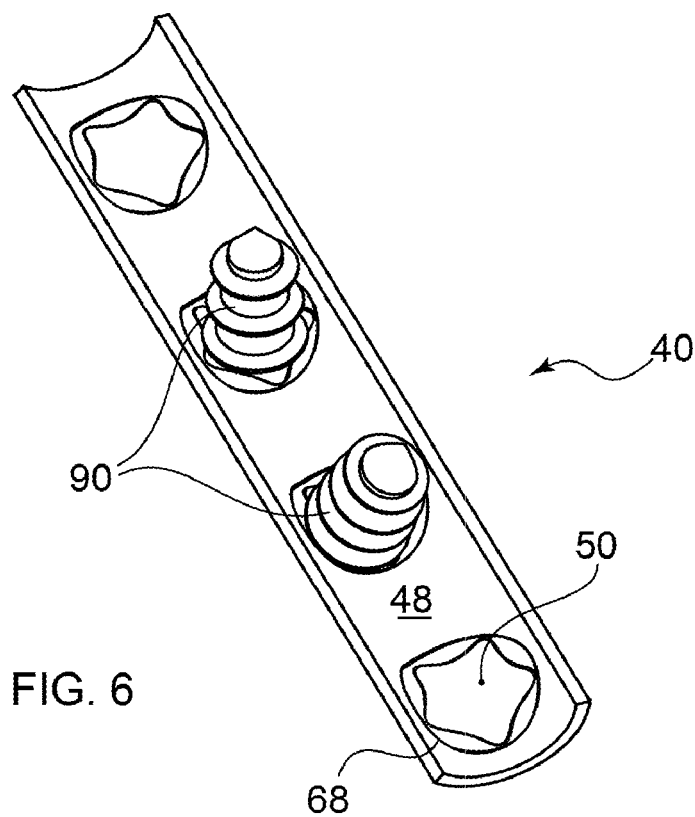
FIG. 6 shows a bottom perspective view of the bone plate of FIG. 5.

As shown in FIG. 6, the lower circumference 68 at the bone contacting surface 42 of plate 40 may appear to be more jagged than the upper circumference 62 at the upper surface 44 due to the fins 56 forming a portion of bone contacting surface 42. The lower circumference 68 can appear almost "flower-like," meaning that each fin 56 appears to form a petal of the lower circumference 68. Alternatively, for the embodiments of FIGS. 9-12, the lower circumference 68 will appear similar to the shape created by fins 56.

Although the figures show a finned opening 50 with about five to eight fins 56, it should be understood that any number of fins 56 is considered within the scope of this invention. For example, there may be two or three fins 56, or ten or twenty or more fins 56, depending upon the plate 40 for which the finned opening 50 is intended for use.

Figure 5:
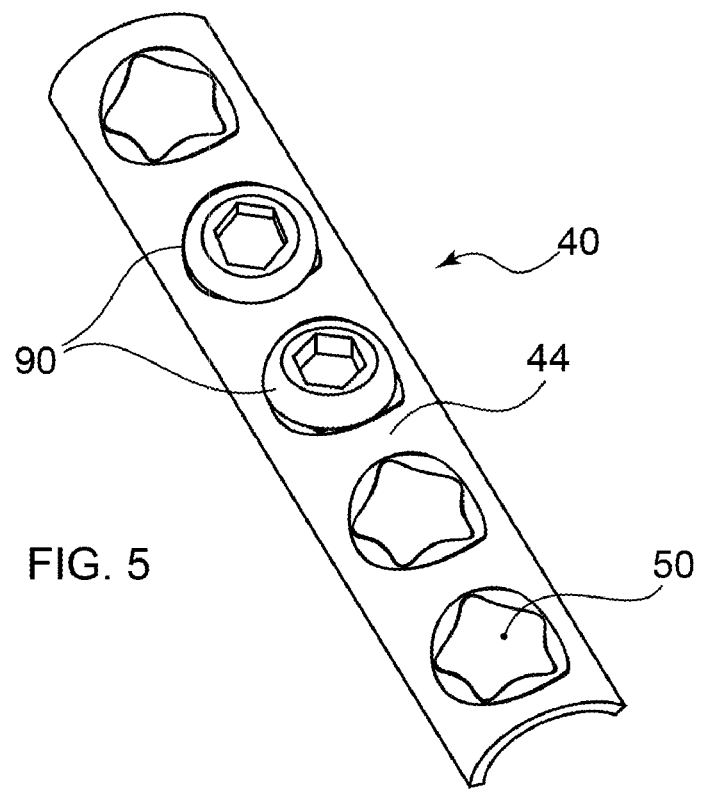
FIG. 5 shows a top perspective view of a bone plate having multiple openings, with fasteners inserted in two of the plate openings.

The primary purpose of fins 56 is to grasp one or more threads 98 of a fastener 90 in order to secure the fastener 90 in place in the bone plate 40 at any desired insertion angle 38. For example, as opposed to threaded openings 30 used with fastener 90 (which engage the threads 98 of the head 94 of the fastener 90 in one way only, limiting the surgeon's ability to angle the fastener 90 as desired), the fins 56 of this embodiment are still intended to secure the threads 98 of the head 94 of fastener 90 in place, but at any insertion angle 38. Moreover, as shown in FIGS. 5-7, fasteners 90 need not be inserted at the same insertion angle 38. One fastener 90 may be inserted at a first insertion angle 38, and another fastener 90 may be inserted at a second, and different, insertion angle 38. As a fastener 90 is inserted, its threads 98 start to engage the fins 56, as shown in FIG. 3. As discussed above, the fins 56 may be very thin so that as the threads 98 start to grab fins 56, the fins 56 may move up or down as appropriate to engage the threads 98 and secure the fastener 90 in the finned opening 50. In short, the threads 98 engage fins 56 so that the fins 56 fit between the threads 98. This movement of fins 56 can be a permanent deformation, so that the fins 56 cannot flex back and allow the fastener 90 to work its way out.

Figure 23:
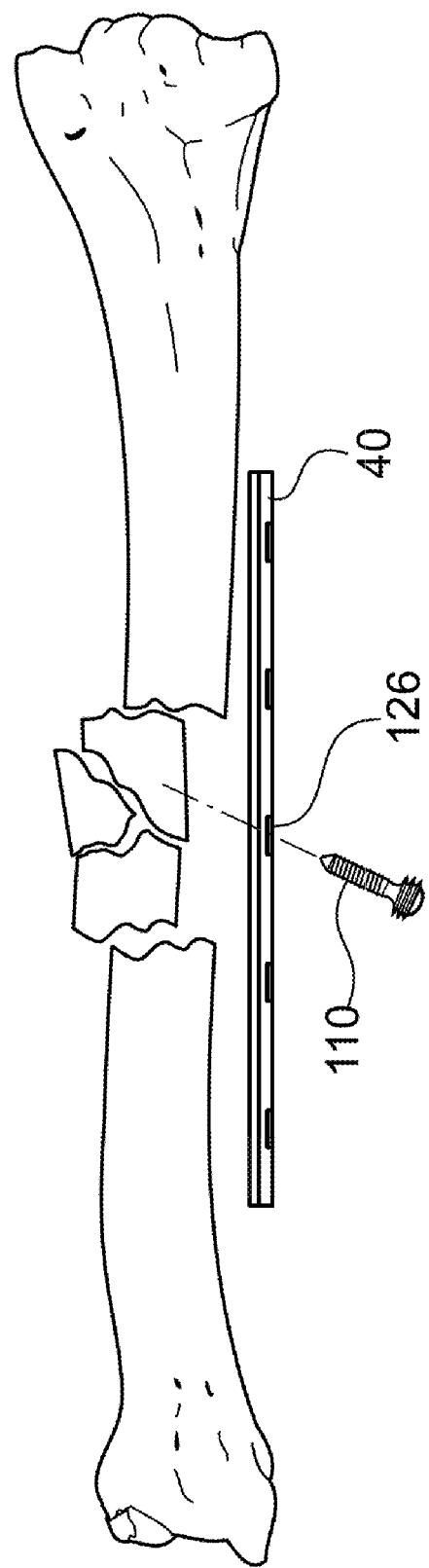
FIG. 23 shows a side elevation view of a fracture being treated with a bone plate and the fastener of FIG. 19.

As discussed above, finned openings 50 may be provided on all types of bone plates 40 and may be combined with other types of openings, examples of which are shown in FIGS. 13-17. There may be a finned opening 50, a threaded opening 30, and a provisional pin opening 102. Other options are holes that can be used with either a threaded or non-threaded fastener, as well as combination slots 104. It should be understood that these various types of openings may be used on any types of bone plates, in any combination and in any size. FIG. 14 shows a plurality of finned openings 50 in the head of bone plate 40. This may help achieve better fixation of a fractured bone, because the fastener 90 can be inserted at various angles to capture "renegade" or random bone fragments that have split from the bone during fracture, but still secure the bone fragments to the plate 40. For example, as shown in FIG. 23 if a bone is broken, there will be numerous fragments that may shatter in various directions. The plates 40 described herein can be used to place a fastener 110 at various angles in order to capture the renegade fragments that would otherwise not be secured to a bone plate 40 using only a locking or a non-locking fastener. Although FIG. 23 shows a fastener 110 with a finned head 112, the same concept applies to a fastener 90 and a finned opening 50. It should additionally be understood that other types of openings (in addition to or instead of finned openings 50) may be present in the head of the plate, as well as elsewhere on plate 40. Particularly suitable may also be openings 30 for receiving fasteners 10, which also allow for polyaxial insertion and fixation.

As previously mentioned, fastener 90 may be any typical fastener, made out of any appropriate material. It will typically have a bore 18 for receiving a driver in order to drive fastener 90 through plate 40 and into bone. The bore 18 may be any size and shape, for example, it may have a hexagonal configuration to receive a corresponding hexagonal driver, a Phillips screw head, a flat-head, a star configuration, Torx, or any other appropriate configuration that can cooperate with a driver to drive fastener 90 into plate 40.

Turning now to the methods of implantation, the surgeon accesses the surgical site of interest, which can be an internal site at which a bone fracture is located that requires stabilization to ensure proper healing. The fracture may be reduced with conventional forceps and guides (which are known to those in the art), and a bone plate 40 of appropriate size and shape is placed over the fracture site. In some instances, the bone plate 40 may be temporarily secured to the bone using provisional fixation pins. In the bone plates 40 shown in FIGS. 13 and 14, provisional fixation pins may be used through either the provisional pin openings 102, or any other opening in the plate 40. Provisional fixation provides for temporarily securing the bone plate 40 to the bone before placing fixation screws through the bone plate 40, so that one can be certain the bone plate 40 is properly positioned before placing bone screws for permanent fixation of the bone plate 40 to the bone. Moreover, with provisional fixation, x-rays can be taken of the bone plate/construct without excess instruments in the field of view.

Once the plate 40 is secured at a desired location in relation to the fracture (typically using one or more provisional fixation pins, although any other appropriate method may be used), the surgeon then identifies an insertion angle 38 (see FIGS. 2 and 7), or the direction along which fastener 10, 90 is to be inserted through a selected opening 30, 50 and driven into bone material. If bone plate 40 includes more than one opening 30, 50 as shown in FIGS. 13-17, the surgeon also selects the specific opening 30, 50 to be used. After selecting the desired insertion angle 38 and opening 30, 50, the surgeon inserts shaft 14, 92 of fastener 10, 90 through opening 30, 50 until the tip contacts bone material. In some cases, a hole may need to be drilled or tapped into the bone along the insertion angle 38 to facilitate the initial tapping or insertion of fastener 10, 90. The surgeon then uses an appropriate driving tool in the bore 18 of head 16, 94 to manipulate the fastener 10, 90 into place.

Because fastener 10, 90 may be inserted at angles other than aligned with the central axis 36, 52 of opening 30, 50, fastener 10, 90 may be used to grab or secure bone fragments that are out of line with the traditional angle at which a locking screw would normally be inserted. The surgeon may need to toggle or maneuver the fastener 10, 90 in order to secure and draw in displaced bone fragments.

Once the bone fragment is secured, the fastener 10, 90 is ready to be secured to the plate 40. As fastener 10, 90 is driven further into bone it is also drawn further into plate 40. If fastener 10 is used in an opening 30, drawing the fastener 10 into the plate 40, for example by rotating the fastener 10 with a tool via the bore 18, causes deformation of the fastener seating surface 20 because the fastener seating surface 20 is made from a material that is weaker than the threads 32 in the opening 30. This deformation allows "threads" to be tapped into the head 16 of the fastener 10 and fixes the orientation of the fastener 10 relative to the opening 30. If fastener 90 is used in finned opening 50, as threads 98 of fastener head 94 begin to contact fins 56, the fins 56 are allowed to engage within the threads 98 to hold the fastener 90 in place in the desired insertion angle 38, even angles that are other than in line with the opening central axis 52. The action of engagement between fins 56 and threads 98 rigidly affixes fastener 90 to the bone plate 40 at the desired insertion angle 38.

In some embodiments, the surgeon may then use traditional locking and/or non-locking screws in other openings 30, 50 on plate 40. This can help further secure the bone plate 40 to the bone fracture if needed. One advantage of opening 30 is that it is adapted to receive a fastener 10, 90, other locking screws, or a non-locking screw.

In some instances, once all fasteners 10, 90 and/or screws are placed, the surgeon may place covers over the unused openings 30, 50 particularly if there are any unused openings 30, 50 that cross the fracture in order to strengthen the plate 40. Additionally or alternatively, the surgeon may use bone graft material, bone cement, bone void filler, and any other material to help heal the bone.

FIGS. 18-22 illustrate an alternate embodiment of an opening and fastener that allows for polyaxial fixation. Plate 40 is provided with openings 126 for receiving fastener 110, as shown in FIGS. 18-22. These figures show a fastener 110 with a finned head 112. Specifically, the finned head 112 comprises a bore 114 and at least one set of extending fins 118 around a portion 120 of the finned head 112. Fins 118 are shown as being square or trapezoidally-shaped with tapered edges, although they may be any other shape, such as rounded, oval, rectangular, curved, rhomboid, diamond-shaped, triangular or any other appropriate shape. The edges of fins 118 may taper inwardly, outwardly, or be about parallel with one another. Fins 118 may be provided in a single row around finned head 112 or layered in multiple rows as shown. If layered in multiple rows, each individual fin 118 may be directly above another fin 118 (so the top of the fastener 110 looks like that shown in FIG. 20). Alternatively, each individual fin 118 in a lower layer may be offset from a fin 118 in a higher layer. The number of fins 118 in a set may also vary from about two or three up to any desired number that can fit on portion 120 of finned head 112. As with the fins 56 of finned opening 50 described above, the fins 118 are preferably quite thin, the thickness varying depending upon the use of fastener 110 and plate 40. For example, a larger fastener 110 for use with a larger plate 40 (e.g., for use on a femur bone) will likely have larger and thicker fins 118 than a smaller fastener 110 (e.g., for use on a smaller bone). In specific embodiments, the fins 118 are particularly thin so that they can be moved up or down or compressed upon pressure. A non-limiting exemplary range of thicknesses for fins 118 may be from about 0.5 mm to about 5 mm, although larger and smaller sizes are possible. In theory, the fins 118 are intended to fit between the threadform of plate 40. Fastener 110 may also have a shaft 122 that is threaded or unthreaded, as described above with respect to fastener 90.

Figure 22:
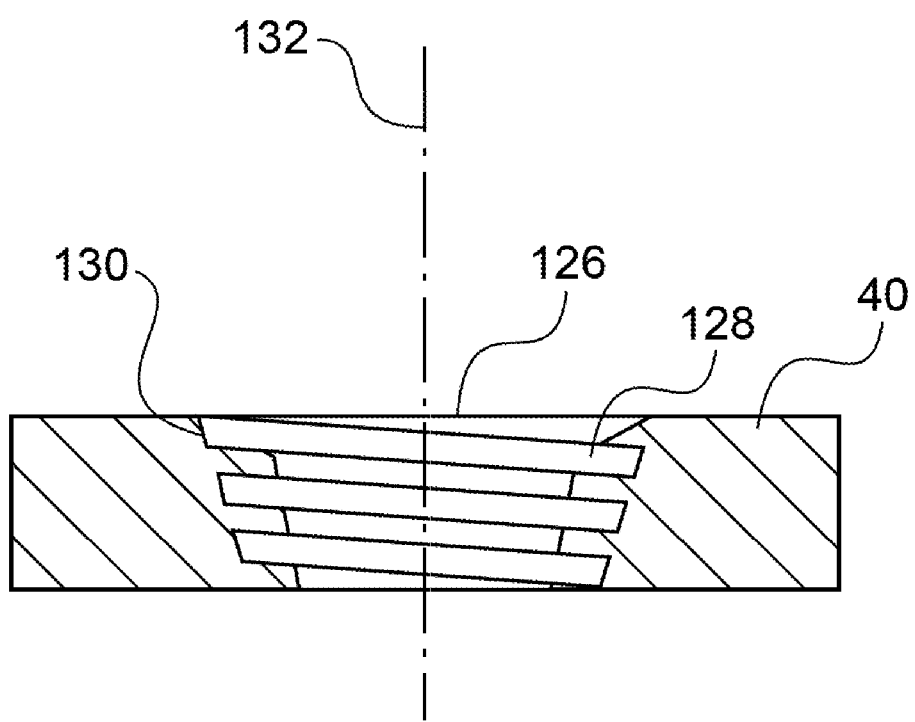
FIG. 22 shows a cross-sectional view of the plate of FIG. 21.

Fastener 110 may be used with any bone plate that has a threaded opening. In one example (see FIGS. 18, 21, and 22), bone plate 40 includes opening 126 provided with Acme threads 128 that have a more rectangular shape than the pointed, sharp threads that are typically used in bone plates. As shown in FIG. 22, opening 126 has threads 128 that end at their edges 130 in a rectangular shape. Providing a rectangular shape with a flatter edge 130 allows a larger channel for the fins 118 to engage. In an even more specific embodiment, the threads 128 may be angled at about 15-20° off of the central axis 132 of opening 126, and even more specifically, at about 18° off of the central axis 132. While Acme threads are disclosed, one of skill in the art will recognize that any thread geometry may be provided in opening 126.

Figure 18:
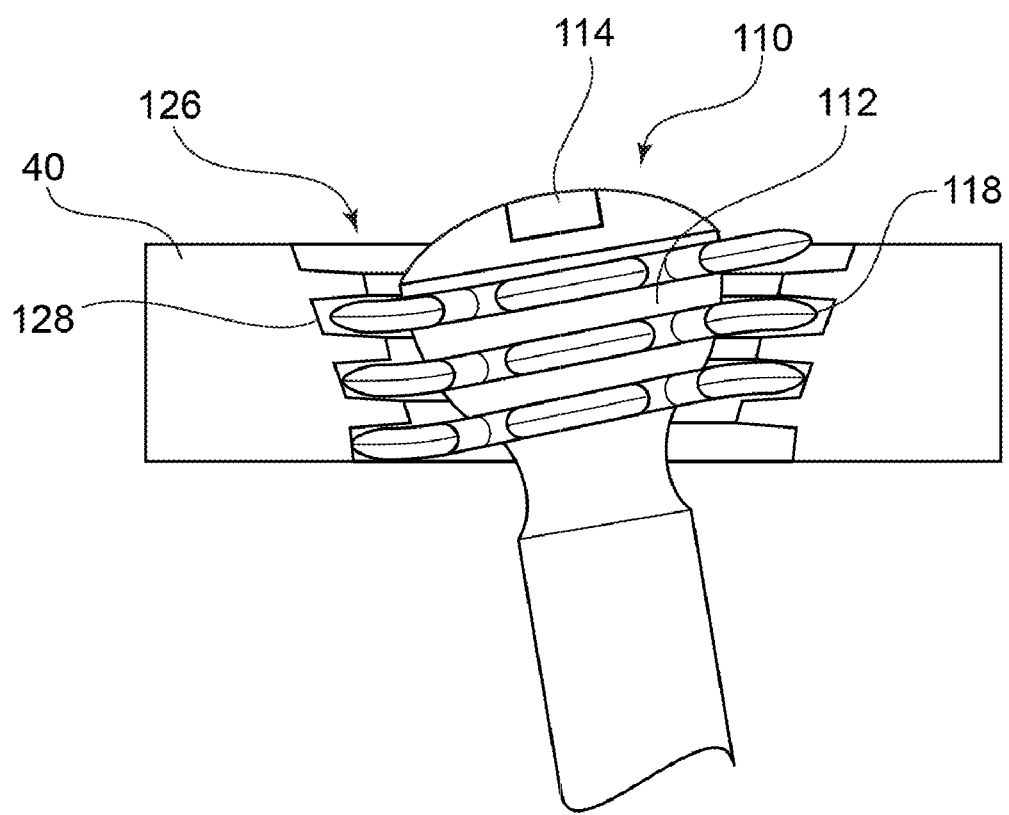
FIG. 18 shows a cross-sectional view of an alternative embodiment of a bone plate having a fastener with a finned head secured in the bone plate.
Figure 19:
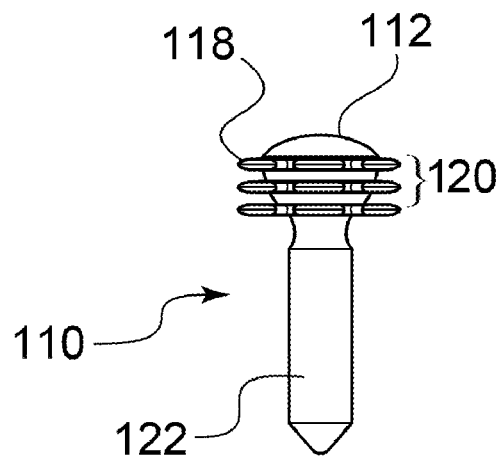
FIG. 19 shows a side elevation view of the fastener shown in FIG. 18.
Figure 20:
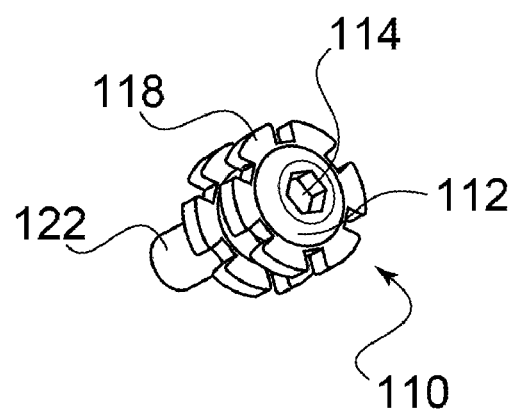
FIG. 20 shows a top perspective view of the fastener of FIG. 19.
Figure 21:
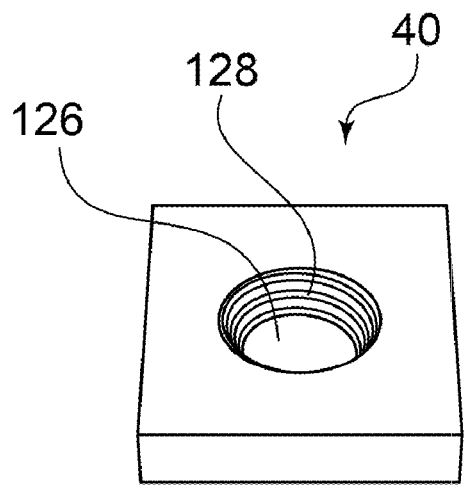
FIG. 21 shows a fragmentary top perspective view of a bone plate that may be used to receive the fastener of FIGS. 19 and 20.

In use, fastener 110 is inserted into opening 126, the fins 118 engage threads 128 and, much like the fins 56, fins 118 are very thin so that as the threads 128 of plate 40 start to grab the fins 118, the fins 118 may move up or down as appropriate to engage the threads 128 and secure the fastener 110 in place, as shown in FIG. 18. In most cases, this movement of fins 118 is a permanent deformation, so that the fins 118 cannot flex back and allow the fastener 110 to work its way out.

Other opening or plate hole geometries that may be provided in plate 40 in any combination are illustrated in FIGS. 25A-E and 30A-C. As discussed in more detail below, these holes or openings may interchangeably receive locking screws or fasteners as well as compression screws or fasteners. They may also receive the fasteners 10 discussed above. Plate 40 may also include non-threaded holes or openings that receive only compression screws or fasteners.

Figure 24A:
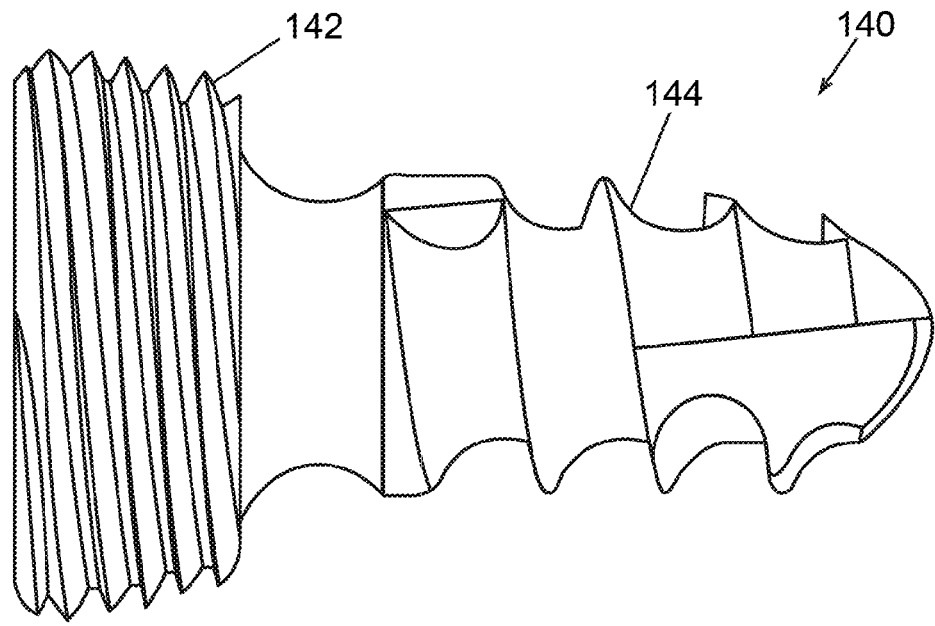
FIG. 24A shows a side elevation view of an exemplary locking screw according to one embodiment of the present invention.
Figure 24B:
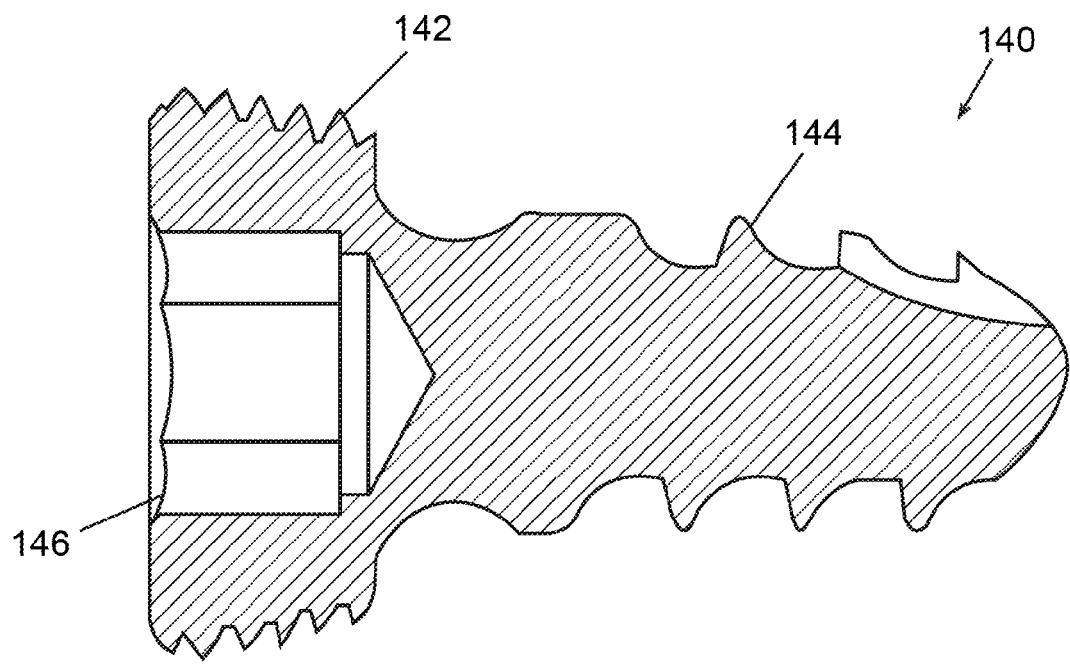
FIG. 24B shows a cross-sectional view of the locking screw of FIG. 24A.

FIGS. 24A and 24B show an exemplary uniaxial locking screw 140 for use according to one embodiment. Such a locking screw 140 includes a threaded head 142 and a threaded shaft 144. Locking screw 140 may be a 3.5 mm, 4.5 mm, 6.5 mm, or other size locking screw, which is understood by those skilled in the art. In the exemplary embodiment shown in FIGS. 24A and 24B, the lead between the threads of head 142 and the threads of shaft 144 is broken. The threads in shaft 144 of locking screw 140 are single lead and the threads in head 142 are triple lead, providing locking screw 140 with the same pitch throughout. It is preferable, but not required, for certain embodiments of locking screws 140 according to this invention to have a constant pitch. In an exemplary 3.5 mm locking screw 140, the pitch is 1.25 mm and the angle of the thread form is about 45° to about 60°. In an exemplary 4.5 mm locking screw 140, the pitch is 1.75 mm and the angle of the thread form is about 60°. Locking screw 140 also includes an internal hex head 146, as shown in FIG. 24B, that is used when tightening locking screw 140 into a bone plate and/or bone.

FIGS. 25A-25E show different views of a portion of a bone plate 40 according to an embodiment of the present invention. Such bone plates generally include one or more holes or other openings, such as in the exemplary bone plates shown in FIGS. 33-50, which are briefly described below. However, for ease of illustration and for purposes of describing an exemplary embodiment of the present invention, only a portion of bone plate 40 is shown in FIGS. 25A-25E.

Figure 25A:
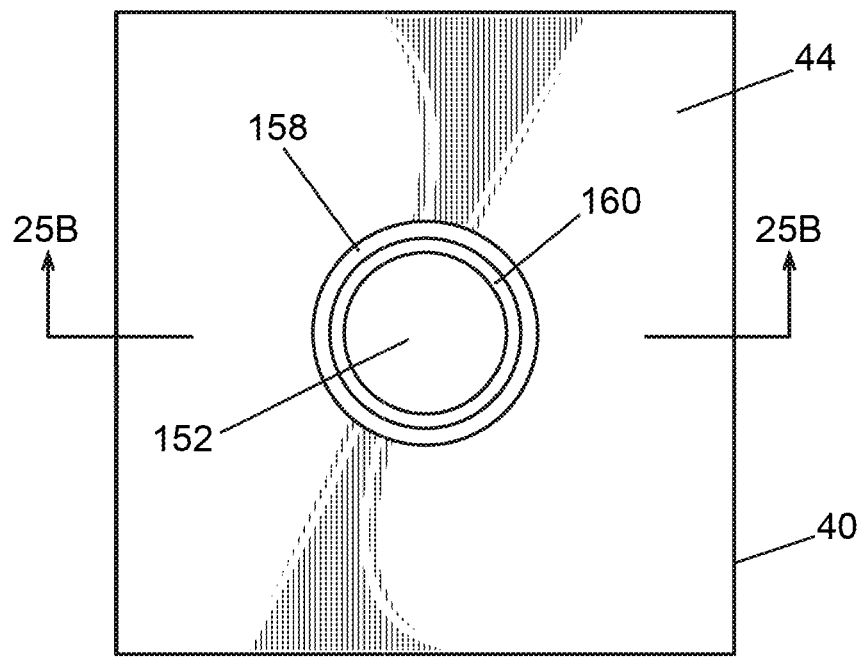
FIG. 25A shows a top plan view of a portion of a bone plate, including a hole without the threads of the hole shown, according to one embodiment of the present invention.
Figure 25B:
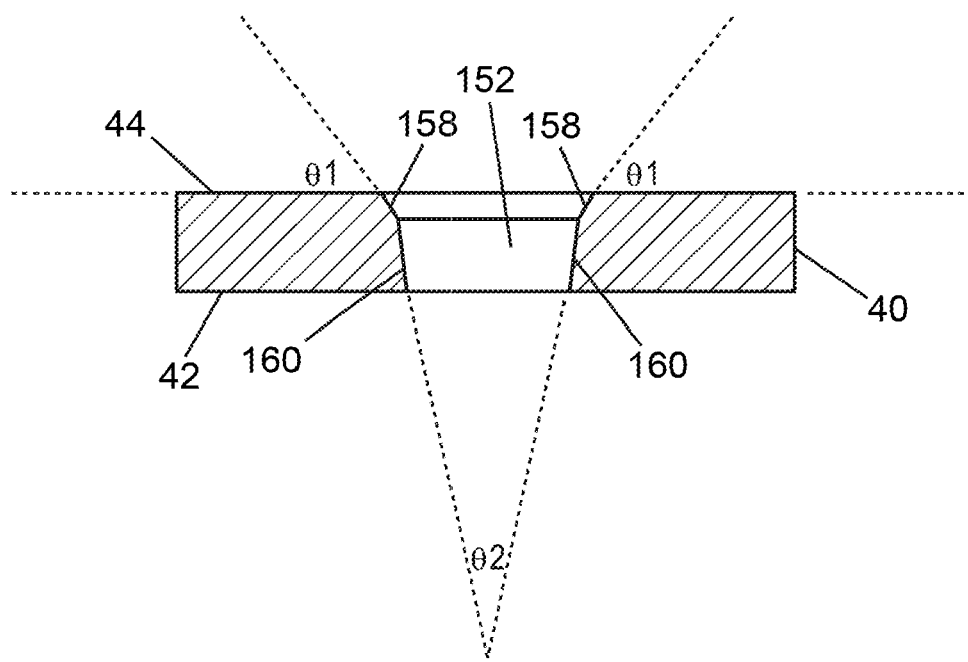
FIG. 25B shows a cross-sectional view of the portion of the bone plate shown in FIG. 25A as viewed along line 25B-25B of FIG. 25A.
Figure 25C:
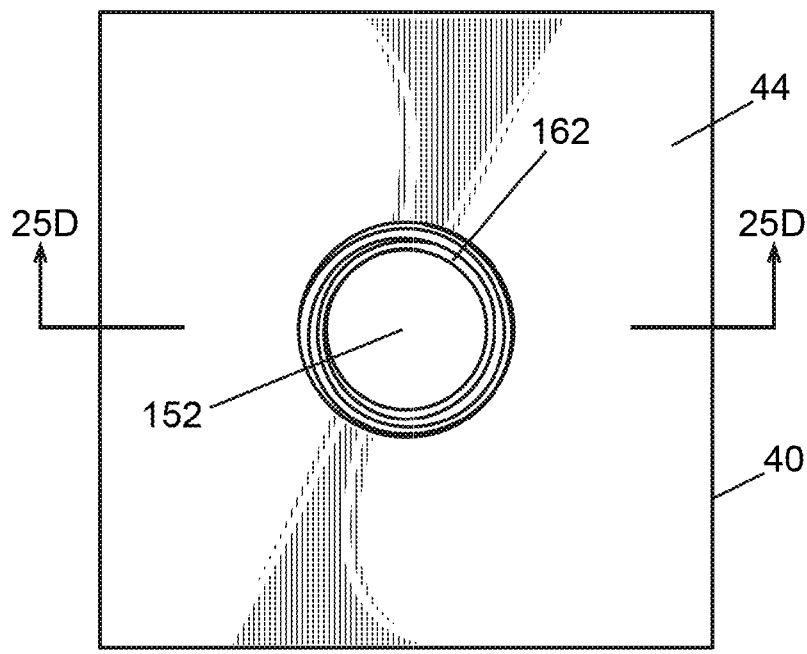
FIG. 25C shows a top plan view of the portion of the bone plate shown in FIGS. 25A and 25B, with the threads of the hole shown.
Figure 25D:
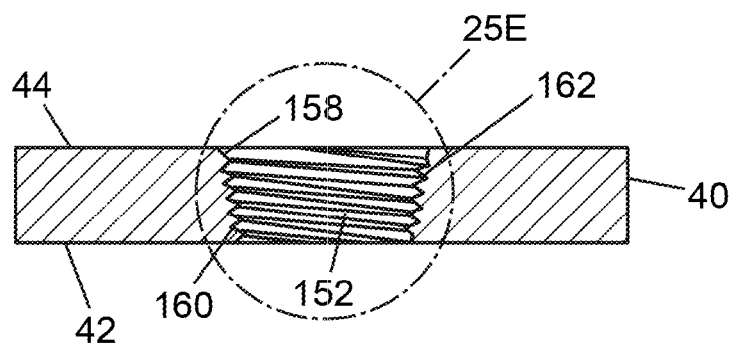
FIG. 25D shows a cross-sectional view of the portion of the bone plate shown in FIGS. 25A-25C as viewed along line 25D-25D of FIG. 25C.
Figure 25E:
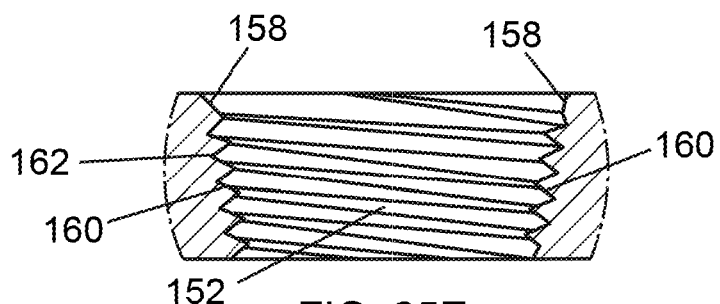
FIG. 25E is an enlarged section view taken at inset circle 25E in FIG. 25D.

The particular bone plate 40 shown in these drawings includes a hole 152 extending through upper surface 44 and bone contacting surface 42 of bone plate 40. FIGS. 25A and 25B show hole 152 without its threads to help illustrate certain aspects of this embodiment of the invention, while FIGS. 25C-25E show hole 152 with its threads. It should be understood that the geometry of hole 152 is the same throughout these Figures, although the geometry of hole 152 is not as clearly visible in FIGS. 25C-E that show the threads of hole 152. As seen most clearly in FIG. 25B, hole 152 includes a top portion 158 extending downward from upper surface 44. Top portion 158 is generally frustoconical in shape and extends from upper surface 44 at an angle of θ1 relative to the plane of upper surface 44, as shown in FIG. 25B. In an exemplary embodiment, angle θ1 is about fifty-two°.

A bottom portion 160 of hole 152 extends from the end of top portion 158 to bone contacting surface 42 of bone plate 40. Bottom portion 160 includes threads 162, as shown in FIGS. 25C-25E. Some of threads 162 may extend into top portion 158 depending on the particular embodiment, but top portion 158 is not completely threaded.

In the exemplary embodiment shown in FIGS. 25A-25E, bottom portion 160 is tapered. The included angle, θ2 shown in FIG. 25B, of the taper of bottom portion 160 may be less than about thirty°, including zero° (i.e., no taper at all). The larger the included angle, the larger hole 152 in bone plate 40 must be, which begins to compromise the strength of the plate if the included angle θ2 is much larger than about thirty°. In an exemplary embodiment, θ2 is about twenty°.

Figure 26:
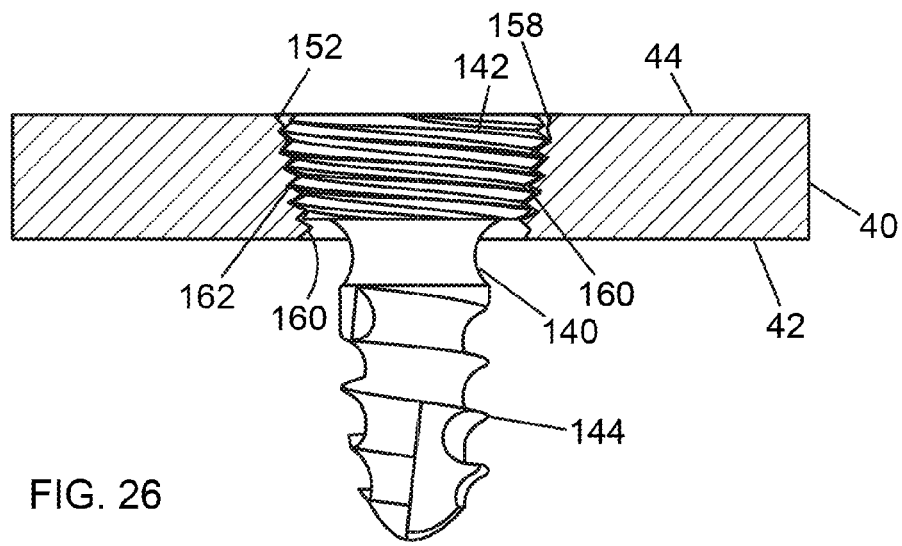
FIG. 26 shows a cross-sectional view of the locking screw of FIGS. 24A and 24B positioned in the bone plate shown in FIGS. 25A-25E.

FIG. 26 shows a side view of locking screw 140 threaded into hole 152 of bone plate 40. Head 142 of locking screw 140 is received by threads 162 of bone plate 40. Threads 162 completely surround the threads of head 142, and the top of head 142 is received completely within hole 152 such that head 142 of locking screw 140 sits flush with upper surface 44 of bone plate 40. Shaft 144 of locking screw 140 is threaded into bone (not shown). Head 142 of locking screw 140 should be tapered such that it properly mates with threads 162 of hole 152 of bone plate 40. Furthermore, a threaded portion of a head of a locking screw for use with certain embodiments of this invention should have a taper generally corresponding to the taper, if any, of the threads of the hole of the bone plate. Fasteners 10 with a seating surface such as shown in FIG. 1 and disclosed above can also be used in the holes 152 to lock and secure the fastener 10 to plate 40 at varying angles within hole 152.

Figure 27:
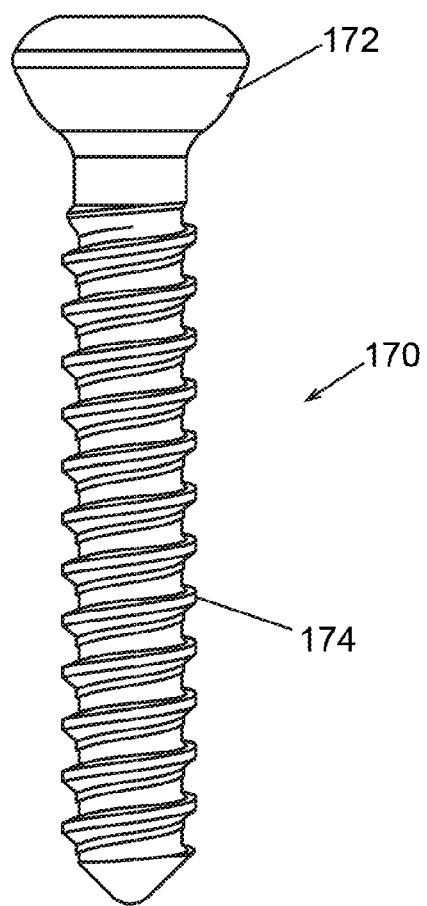
FIG. 27 shows a side elevation view of an exemplary compression screw for use according to one embodiment of the present invention.
Figure 28:
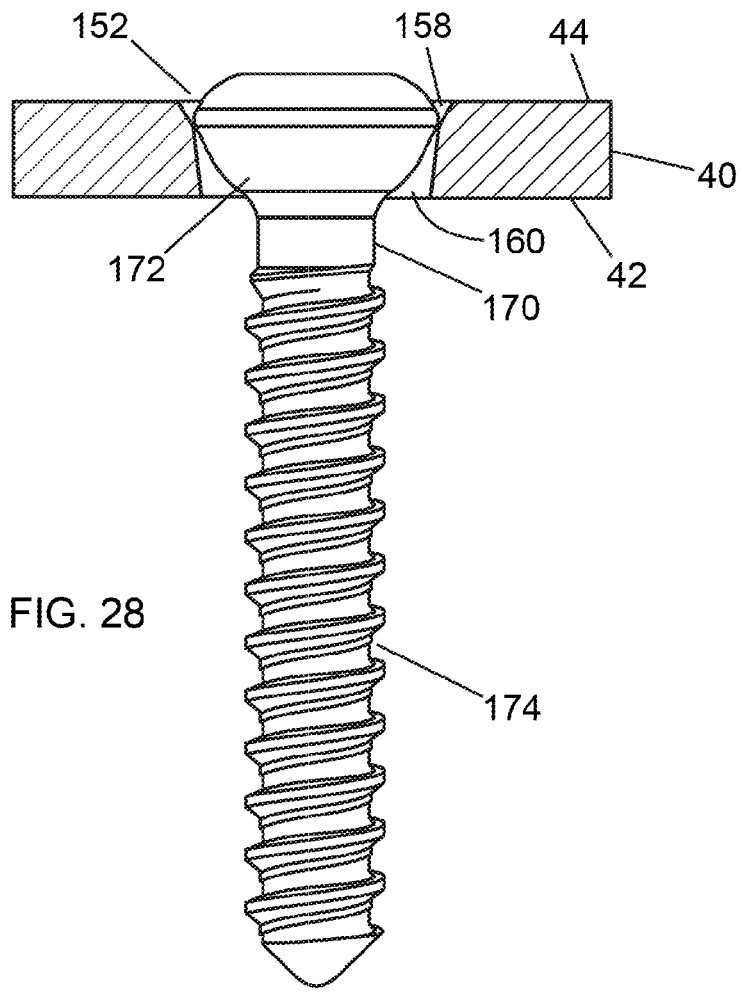
FIG. 28 shows a cross-sectional view of the compression screw of FIG. 27 positioned in the bone plate shown in FIGS. 25A-25E.

FIG. 27 shows a side view of an exemplary compression screw 170 for use according to an embodiment of the present invention. Compression screw 170 includes a head 172 and a threaded shaft 174 for engaging a bone. Head 172 is preferably spherical, as shown in the drawings. FIG. 28 shows compression screw 170 inserted within hole 152 of bone plate 40. As shown in FIG. 28, head 172 of compression screw 170 rides along top portion 158 of hole 152. As shown clearly in FIG. 28, the diameter of shaft 174 is less than the diameter of the opening at bottom portion 160 of hole 152. Thus, as shaft 174 is threaded into a bone (not shown), compression screw 170 may pull or push bone plate 40 in a particular direction as the spherical head 172 of compression screw 170 comes into contact with and rides along the top portion 158 of hole 152 of bone plate 40. The angle θ1, shown in FIG. 25B, at top portion 158 of hole 152 is significant for compression of a fracture and is necessary to help shift the bone plate in the desired direction. If top portion 158 were to extend straight down from upper surface 44 of bone plate 40, compression would be less successful. Compression screw 170 may move bone plate 40 in more than one direction as compression screw 170 is fully inserted within hole 152. In an exemplary embodiment, fine adjustment of fractures up to about two millimeters in several directions is possible.

Figure 29A:
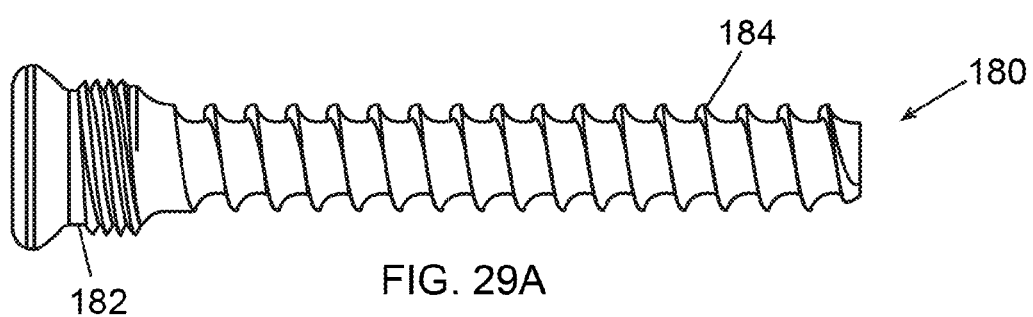
FIG. 29A shows a side elevation view of an exemplary locking screw according to an embodiment of the present invention.
Figure 29B:
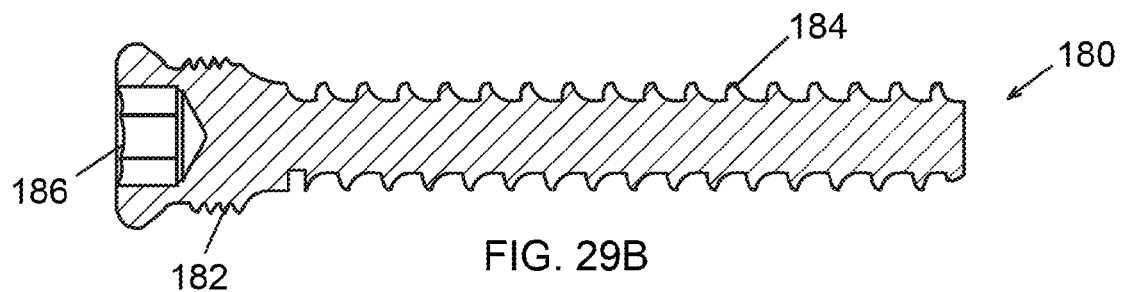
FIG. 29B shows a cross-sectional view of the locking screw of FIG. 29A.

FIGS. 29A and 29B show another exemplary locking screw for use according to an embodiment of the present invention. A locking screw 180 includes a head 182 and a threaded shaft 184. Similar to locking screw 140 shown in FIGS. 24A and 24B, locking screw 180 may be a 3.5 mm, 4.5 mm, 6.5 mm, or other size locking screw, which is understood by those skilled in the art, and the lead between the threads of head 182 and the threads of shaft 184 is broken. The threads in shaft 184 of locking screw 180 are single lead and the threads in head 182 are triple lead, providing locking screw 180 with the same pitch throughout. The pitches and angles of thread form for exemplary 3.5 and 4.5 mm locking screws 180 are generally similar to those described above with reference to locking screw 140.

Locking screw 180 also includes an internal hex head 186, as shown in FIG. 29B, that is used when tightening locking screw 180 into a bone plate and/or bone. As may be seen from FIGS. 24 and 29, only a portion of head 182 of locking screw 180 is threaded, whereas the entire head 142 of locking screw 140 is threaded. Additionally, the threaded portion of head 182 of locking screw 180 is not tapered, while head 142 of locking screw 140 is tapered. These differences are because locking screw 140 is designed to mate with hole 152 of bone plate 40, while locking screw 180 is designed to mate with a hole 192 of a bone plate 40, as further described below.

Figure 30A:
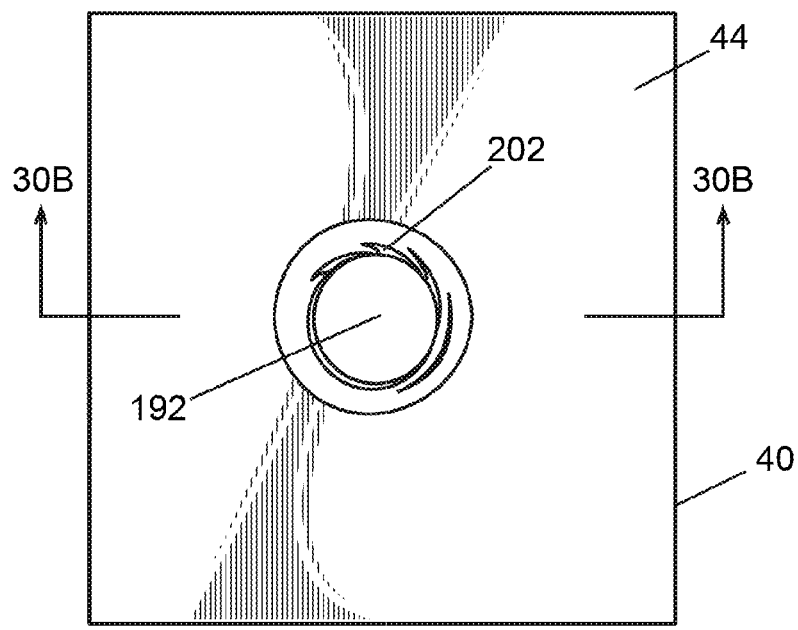
FIG. 30A shows a top plan view of a portion of a bone plate according to an embodiment of the present invention.
Figure 30B:
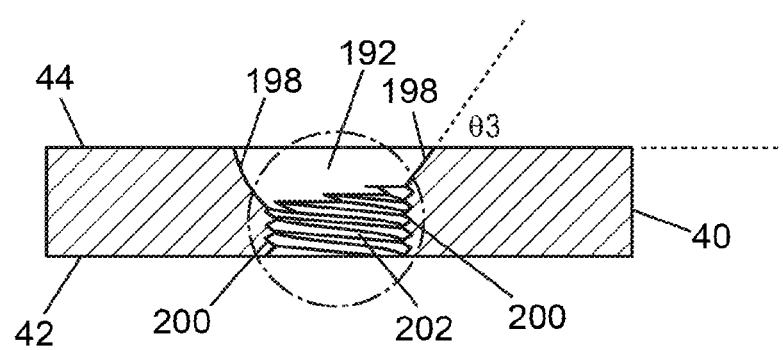
FIG. 30B shows a cross-sectional view of the portion of the bone plate shown in FIG. 30A as viewed along line 30B-30B of FIG. 30A.
Figure 30C:
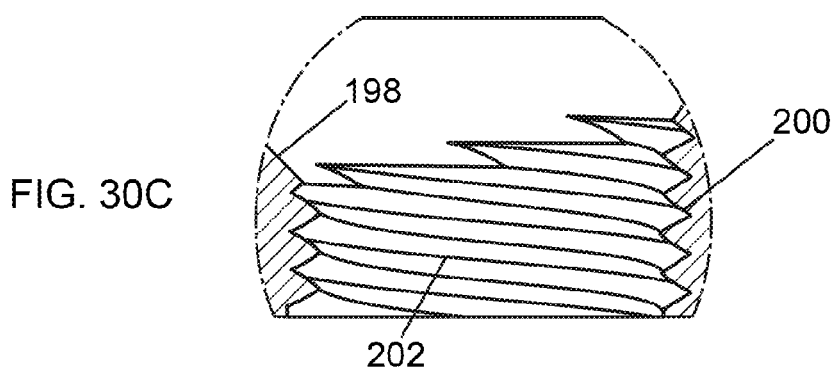
FIG. 30C is an enlarged section view taken at inset circle 30C in FIG. 30B.

FIGS. 30A-30C show different views of a portion of a bone plate according to an embodiment of the present invention. As noted above, bone plates generally include one or more holes or other openings, such as in the exemplary bone plates shown in FIGS. 33-50, but for ease of illustration, only a portion of bone plate 40 is shown in FIGS. 30A-30C.

Bone plate 40 includes a hole 192 extending through upper surface 44 and bone contacting surface 42 of bone plate 40. Hole 192 includes a top portion 198 extending downward from upper surface 44. As shown in FIG. 30B, one side of top portion 198 includes a ramp that extends from upper surface 44 at an angle of θ3 relative to the plane of upper surface 44. In an exemplary embodiment, angle θ3 is about fifty-two°. The remainder of top portion 198 is a concave recessed portion that is generally spherical in shape, as shown in FIG. 30B.

Although of a slightly different structure than top portion 158 of hole 152, top portion 198 of hole 192 also has a generally frustoconical shape, as shown in the figures.

A bottom portion 200 of hole 192 extends from the end of top portion 198 to bone contacting surface 42 of bone plate 40. Bottom portion 200 includes threads 202. Some of threads 202 may extend into top portion 198 depending on the particular embodiment, but top portion 198 generally has only the beginning of thread leads, if any threading. Unlike bottom portion 160 as shown in FIGS. 25A-25E, bottom portion 200 in FIG. 30B is not tapered, but rather is generally cylindrical in shape.

Figure 31:
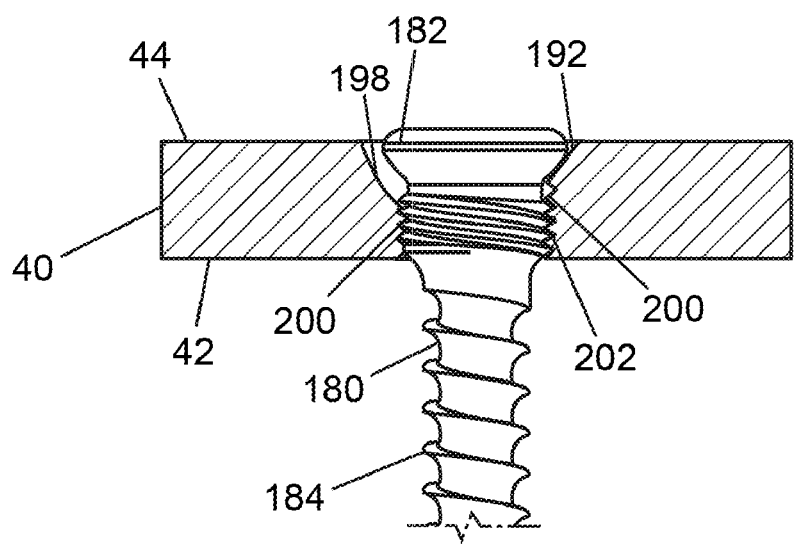
FIG. 31 shows a cross-sectional view of the locking screw of FIGS. 29A and 29B positioned in the bone plate shown in FIGS. 30A-30C.

FIG. 31 shows a side view of locking screw 180 threaded into hole 192 of bone plate 40. Threads of head 182 of locking screw 180 are received by threads 202 of bone plate 40. Threads 202 completely surround the threads of head 182, and shaft 184 of locking screw 180 is threaded into bone (not shown). Head 182 of locking screw 180 is shaped such that its unthreaded portion bears against the ramp of top portion 198 of hole 192 of bone plate 40. Additionally, the threaded portion of head 182 is generally cylindrical (i.e., not tapered) so that it properly mates with threads 202 of hole 192 of bone plate 40. A threaded portion of a head of a locking screw for use with certain embodiments of this invention should be shaped to generally correspond to the shape of the threaded portion of the hole of the bone plate.

Figure 32:
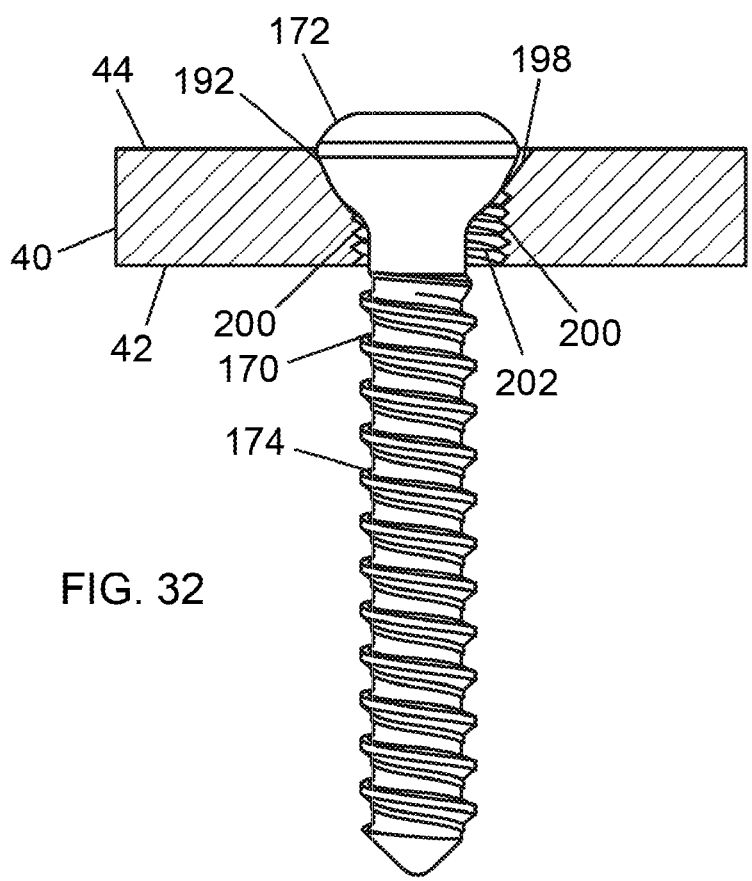
FIG. 32 shows a cross-sectional view of the compression screw of FIG. 27 positioned in the bone plate shown in FIGS. 30A-30C.

FIG. 32 shows compression screw 170 inserted within hole 192 of bone plate 40. As shown in FIG. 32, head 172 of compression screw 170 sits within the frustoconical top portion 198, contacting the concave recessed area of top portion 198 of bone plate 40. Head 172 of compression screw 170 contacts the ramp area of top portion 198, but head 172 does not completely abut the ramp. As shown clearly in FIG. 32, the diameter of shaft 174 is less than the diameter of the opening at bottom portion 200 of hole 192. Thus, as shaft 174 is threaded into a bone (not shown), compression screw 170 may pull or push bone plate 40 in a particular direction as spherical head 172 of compression screw 170 comes into contact with and rides along the frustoconical top portion 198 of hole 192 of bone plate 40, similar to that described above with reference to FIG. 28. The angle θ3, shown in FIG. 30B, at top portion 198 of hole 192 is significant for compression of a fracture and is necessary to help shift the bone plate in the desired direction. If top portion 198 were to extend straight down from upper surface 44 of bone plate 40, compression would be less successful. Compression screw 170 may move bone plate 40 in more than one direction as compression screw 170 is fully inserted within hole 192. In an exemplary embodiment, fine adjustment of fractures up to about two millimeters in several directions is possible.

In practice, a first screw is initially inserted through a bone plate and into a bone on one side of a fracture and then a second screw is inserted through the bone plate on the opposite side of the fracture. In an exemplary method according to an embodiment of the present invention, after the first screw is in place, a compression screw is inserted through a hole in the bone plate on a side of the fracture opposite the side of the first screw. The compression screw may be inserted through the hole and into the bone such that as the compression screw is fully inserted, the bone plate is drawn over to a desired position. By moving the bone plate, the tissue is being pulled together to reduce the fracture. Once the compression screw has been used to move the bone plate into the desired position, the compression screw may be removed from the bone and bone plate and a locking screw, which may, if desired be polyaxial (such as fastener 10), may be inserted through the hole in the bone plate and in the bone in the space formerly occupied by the compression screw. The locking screw can then be tightened to lock the plate into position. The replacement of the compression screw with the locking screw is not required, but a locking screw may provide more stability and rigid fixation than leaving the compression screw in place. In some modes of operation, a locking screw, which may be polyaxial (such as fastener 10), is placed directly in a locking hole without first inserting a compression screw in the hole. Certain embodiments of the invention contemplate using locking screws, some or all of which may be polyaxial or non-polyaxial, and compression screws in any order and in combination or not in combination with each other. As described above, certain embodiments of this invention provide for fine adjustment of fractures in more than one direction.

FIGS. 33-50 show various exemplary bone plate configurations that may include one or more openings or holes of any of the various geometries disclosed herein in any combination for receiving any of the various fasteners or screws disclosed herein. Bone plates in accordance with embodiments of this invention can include threaded, non-threaded, and/or finned openings 50 in any combination. Traditional locking screws 140, compression screws 170, and polyaxial fasteners 10 may be used with such holes as appropriate. All holes in the exemplary plates of FIGS. 33-50 include threads having any of the geometries disclosed herein or fins (not shown), while the other generally non-circular openings in these plates may or may not include threads depending on the purposes for which the opening is to be used.

Figure 33:
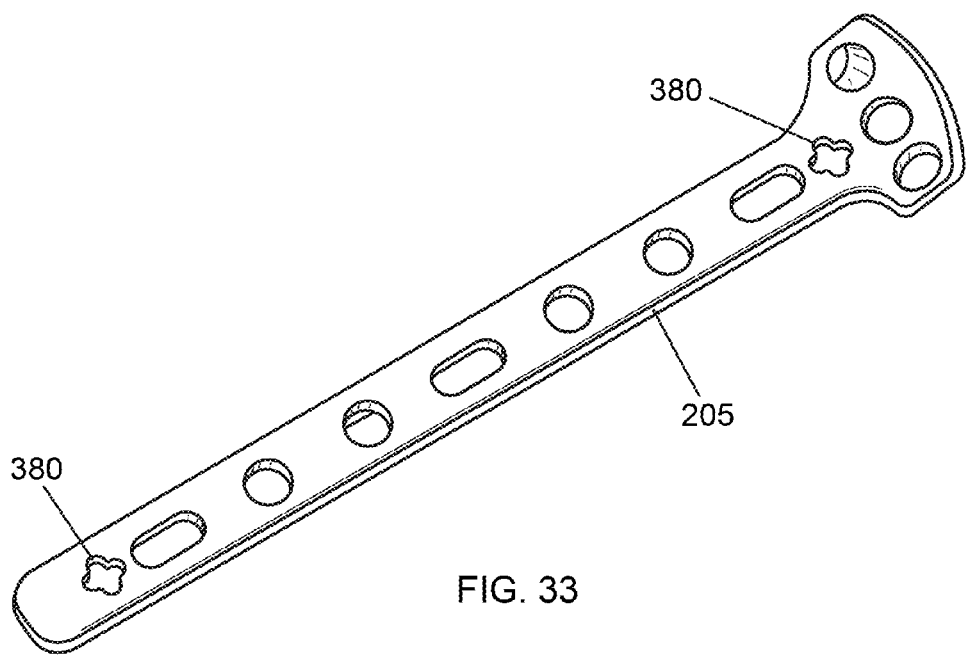
Figure 34:
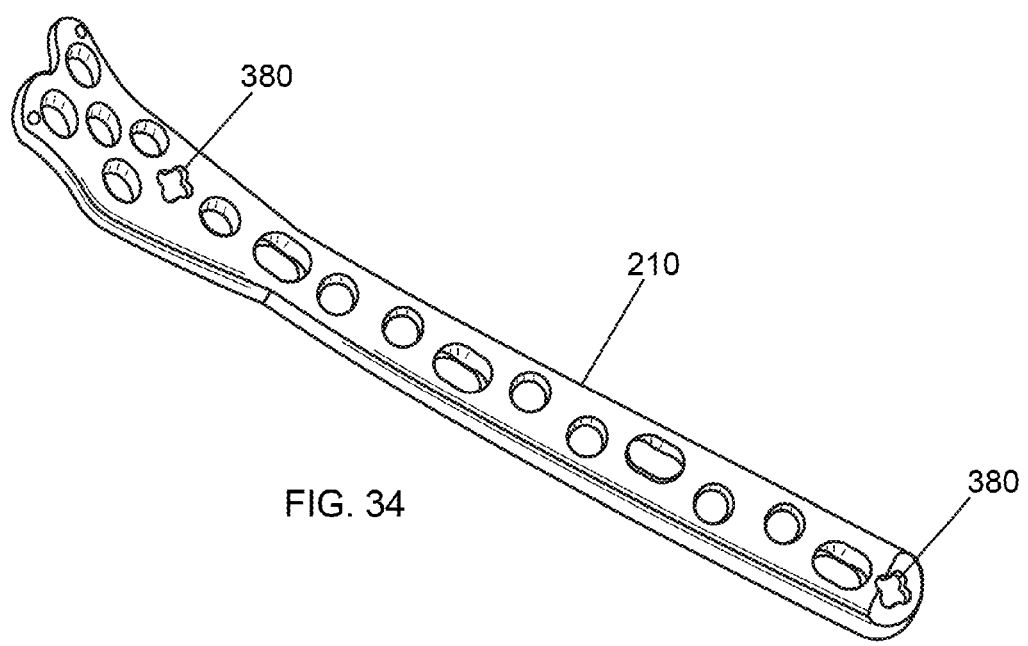
Figure 35:
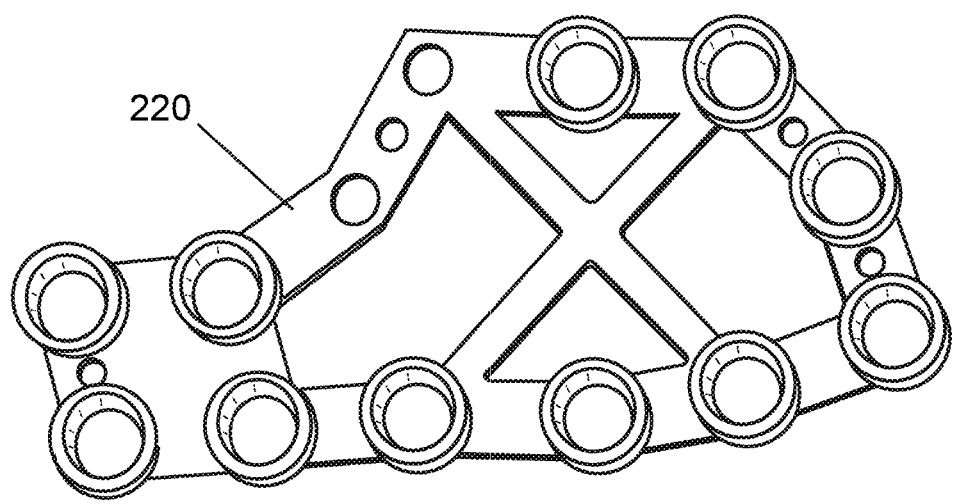
Figure 36:
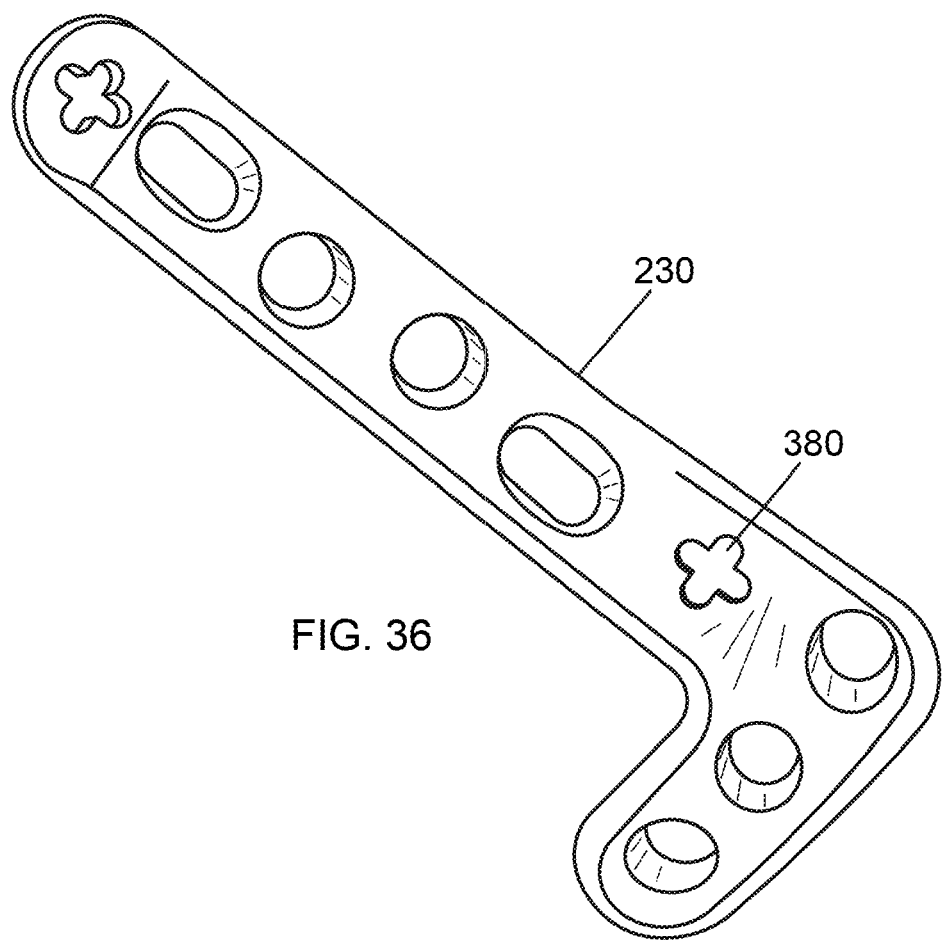
Figure 37:
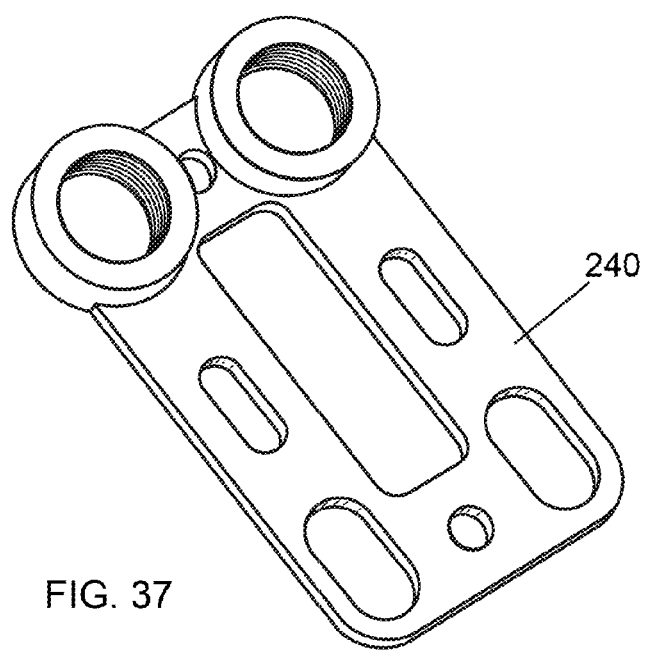
Figure 38:
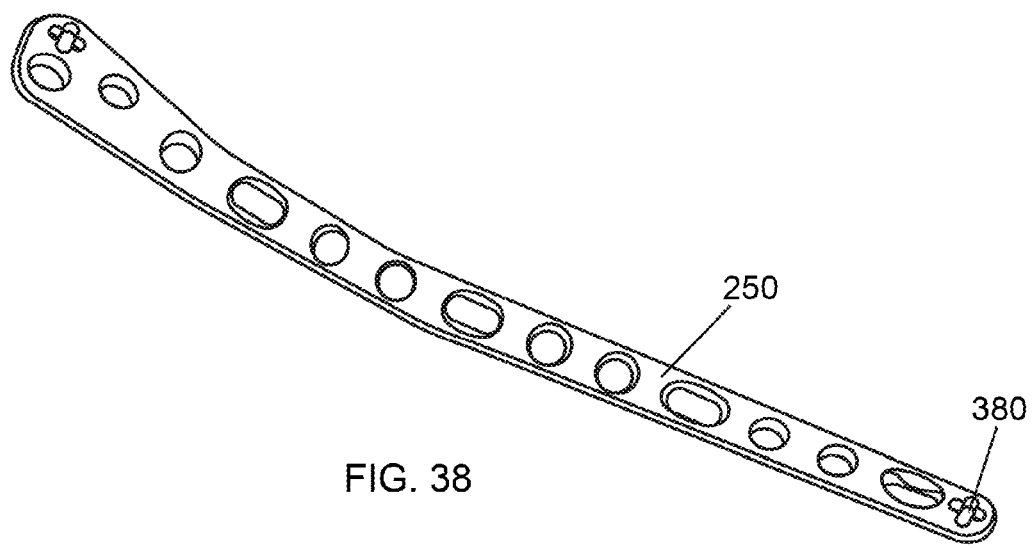
Figure 39:
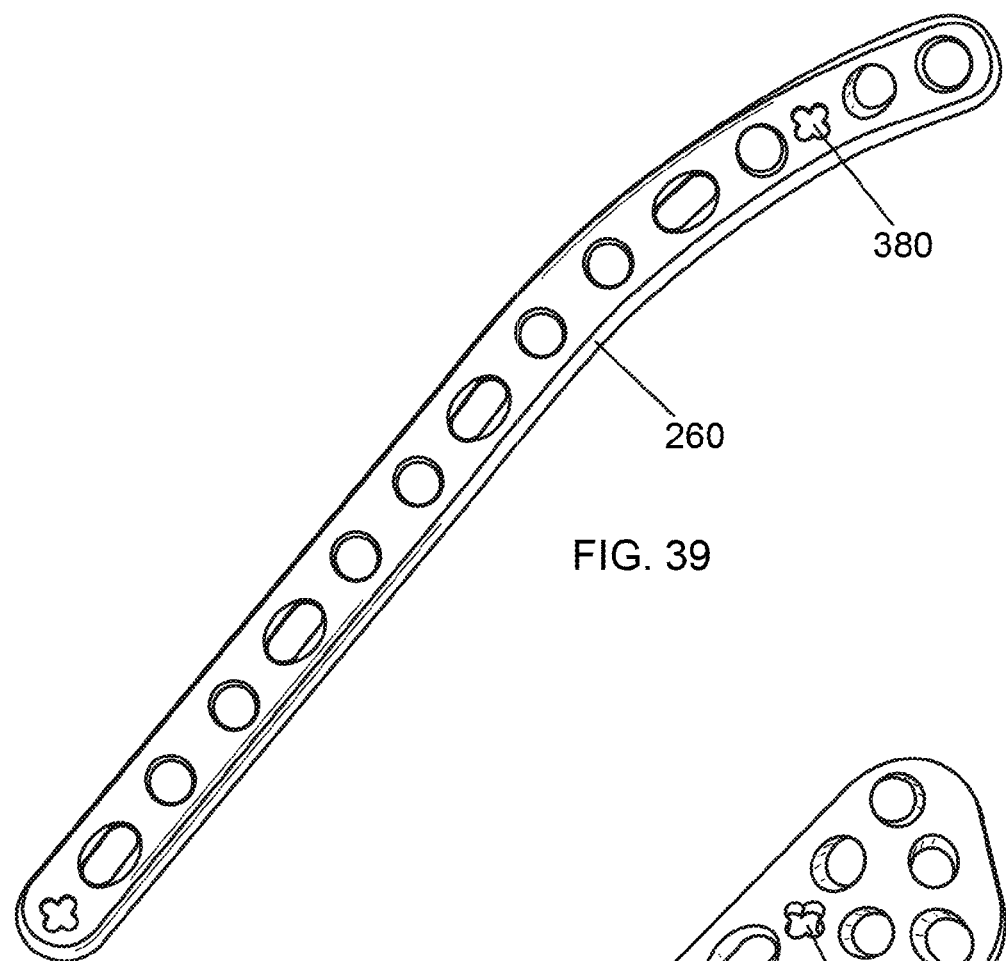
Figure 40:
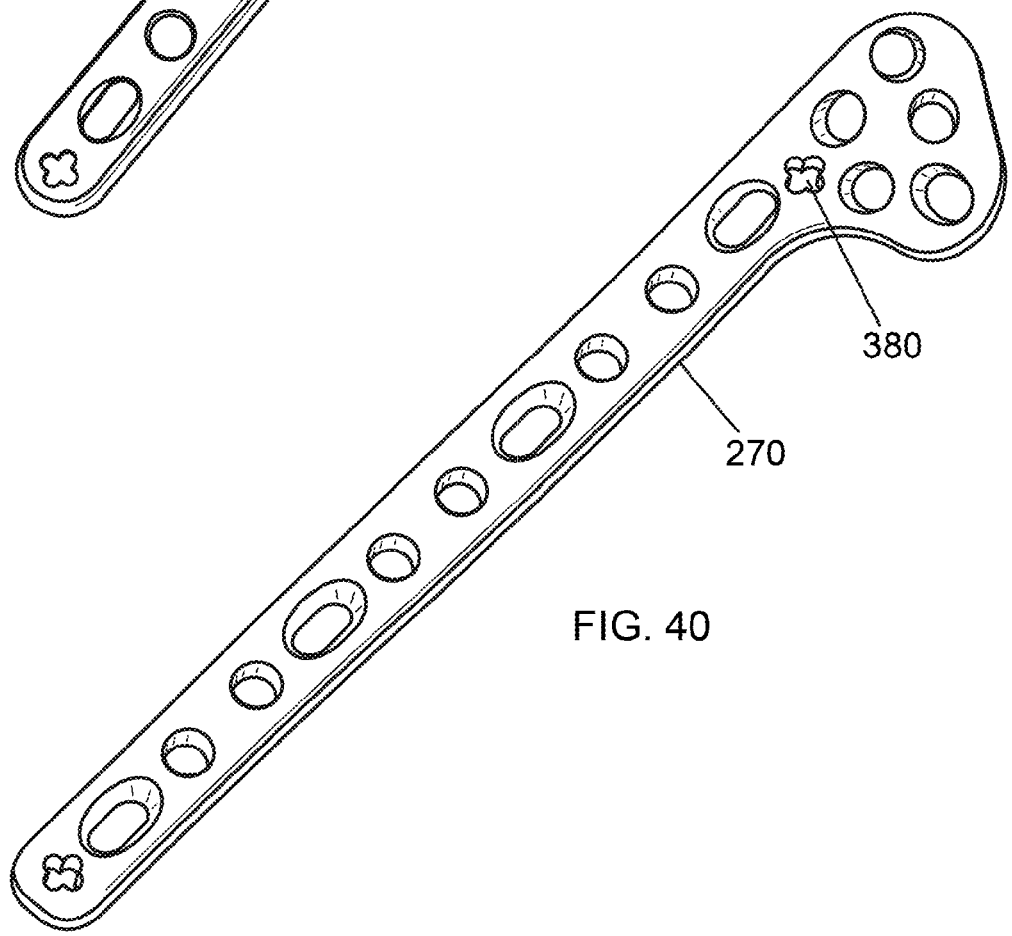
Figure 41:
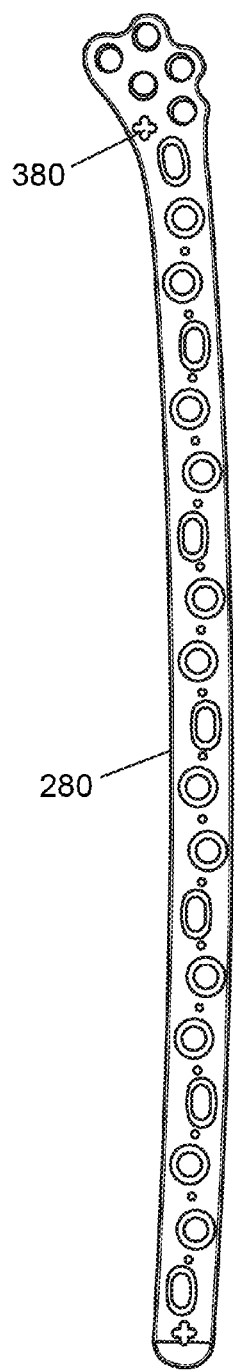

FIG. 33 shows a distal radius plate 205 that is applied on the volar aspect of the radius and used to treat fractures of the distal radius. FIG. 34 shows a distal tibia plate 210 used to treat distal tibia fractures and contoured to match the anatomy of the medial distal tibia. FIG. 35 shows a calcaneal plate 220 that is applied to the medial aspect of the calcaneus and used to treat calcaneal fractures. FIG. 36 shows a distal tibia plate 230 used to threat distal tibia fractures and contoured to match the anatomy of the lateral anterior distal tibia. FIG. 37 shows a multipurpose plate 240 used in conjunction with the calcaneal plate to fuse the talus to the calcaneus. FIG. 38 depicts a distal fibula plate 250 used to treat distal fibula fractures from the lateral side of the bone. FIG. 39 illustrates a bone plate 260 used to treat the medial distal humerus. FIG. 40 shows a proximal humerus plate 270 contoured to match the anatomy of the lateral proximal humerus. FIG. 41 illustrates a distal femur plate 280 contoured to treat fractures of the distal femur from the lateral side of the bone.

Figure 42:
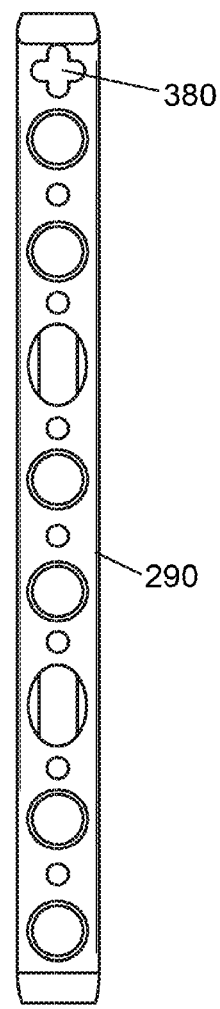
Figure 43:
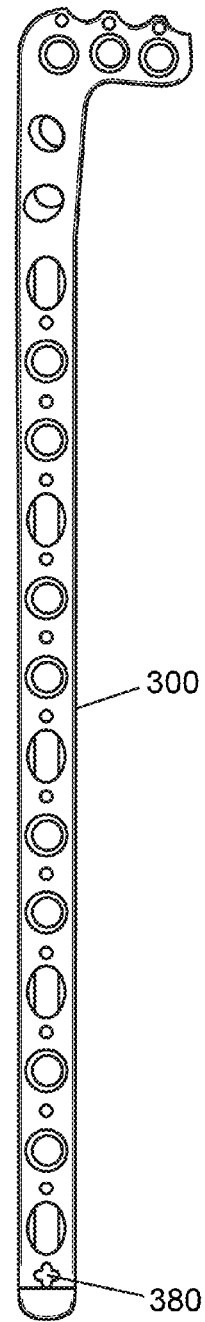
Figure 47:
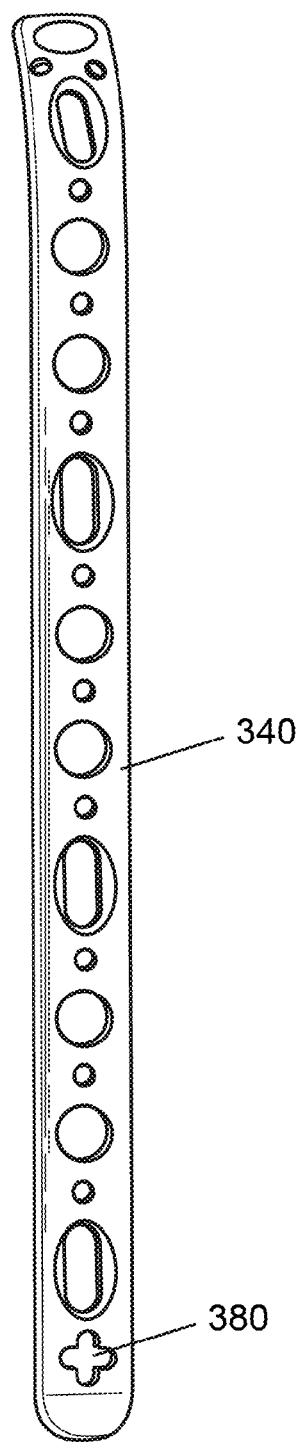
Figure 48:
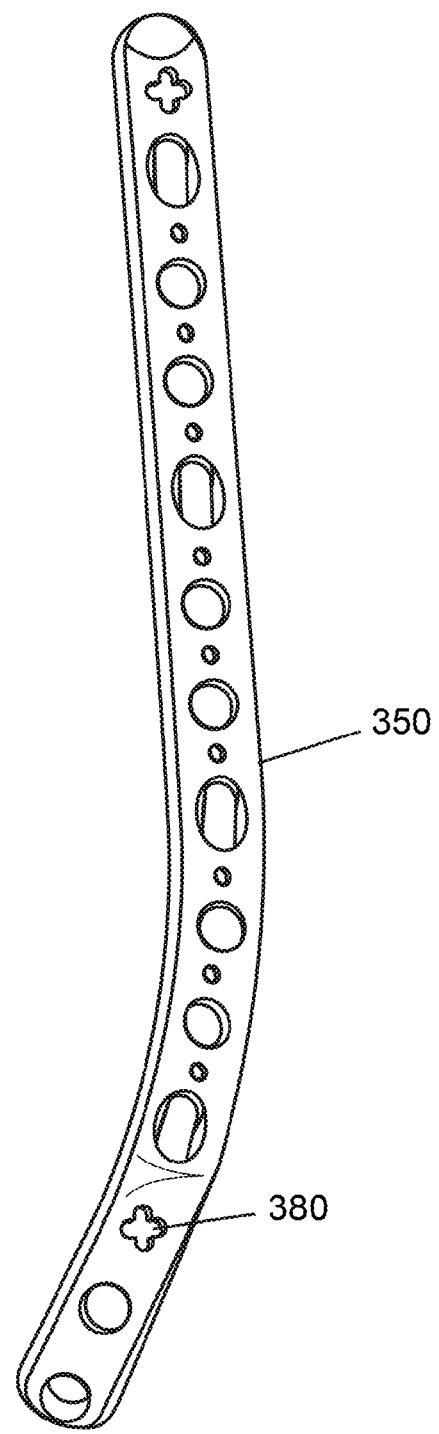
Figures 49, 50, 51:
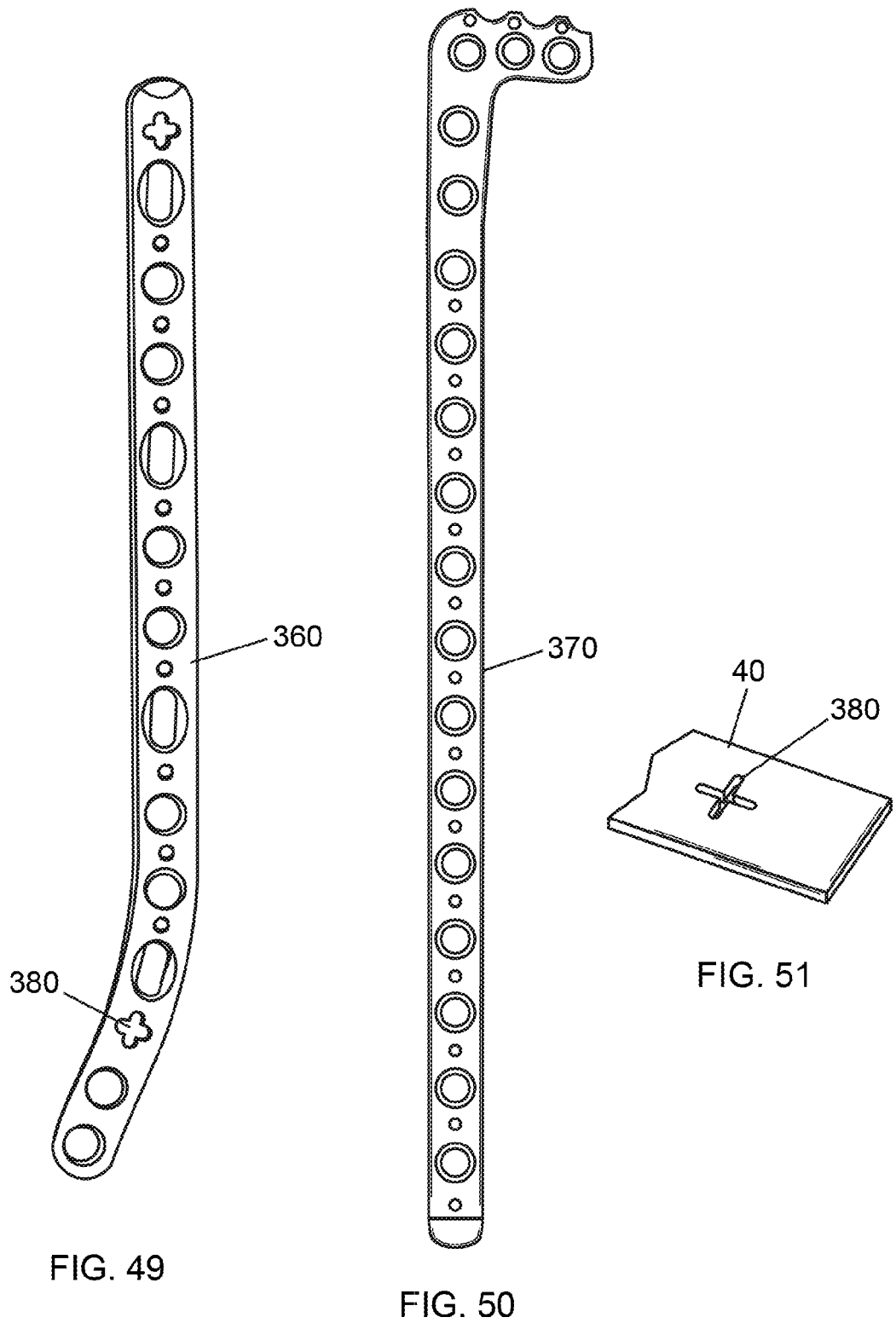

FIG. 42 shows a ⅓ tubular straight bone plate 290 used to treat small bone fractures. FIG. 43 depicts a proximal tibia plate 300 contoured to treat proximal tibia fractures from the medial side. FIG. 44 shows a reconstruction plate 310. FIG. 45 illustrates a small fragment straight plate 320, and FIG. 46 illustrates a large fragment bone plate 330. FIG. 47 illustrates an olecranon plate 340 used to treat fractures of the proximal ulna. FIG. 48 shows a distal humerus plate 350 contoured to match the anatomy of the lateral posterior distal humerus. FIG. 49 depicts a distal humerus plate 360 contoured to match the anatomy of the lateral distal humerus. FIG. 50 shows a proximal tibia plate 370 contoured to treat proximal tibia fractures from the medial side that is similar to plate 300, except that plate 370 includes only holes, such as holes 152 and 192 (shown in more detail in FIGS. 25 and 30, respectively) that may receive both compression and locking screws and does not include any other openings.

Shown in some of the exemplary bone plates in FIGS. 33-50 are provisional fixation slots 380. FIG. 51 shows provisional fixation slot 380 in a portion of a bone plate 40. As is well known to those skilled in the art, provisional fixation pins are commonly used to provisionally affix a bone plate to the bone prior to installation of the bone plate with permanent attachment, such as bone screws. Existing provisional fixation slots typically allow only fixation of bone fragments and not any adjustability of the position of bone fragments. An embodiment of a provisional fixation slot of this invention allows articulation of bone fragments in up to six degrees of freedom to reduce the bone fracture. A bone fragment may be locked into a position and then incrementally repositioned to another temporary or permanent location. In FIG. 51, slot 380 has a cross or X shape, but the shape of slot 380 may vary according to the desired functionality and may include I, L, T, and other shape slots.

In practice, a bone plate is placed on the bone and the plate may or may not be affixed to the bone utilizing bone screws and/or provisional fixation pins. When provisional fixation is desired, a provisional fixation pin may be inserted through a provisional fixation slot and driven into the target bone fragment. The fragment may be manipulated to reduce the fracture and draw the fragment to the plate. Once the bone fragment is in a desired position, the provisional fixation pin may be tightened until the pin locks into the plate. If further movement of the bone fragment is desired, a second provisional fixation pin may be inserted in the same provisional fixation slot in a space in the slot that is not occupied by the first pin. After insertion of the second pin, the first pin may be removed and the bone fragment may be manipulated with the second pin. Once a desired position of the bone fragment is reached, the second pin is locked into the bone plate. Standard devices well known to those skilled in the art, such as screws, pins, cables, and other devices, may be used to affix the bone to the bone plate. Once the construct is sufficiently stable, any provisional fixation pins in use may be removed from the bone.

The foregoing description of exemplary embodiments of the invention has been presented only for the purposes of illustration and description and is not intended to be exhaustive or to limit the invention to the precise forms disclosed. Many modifications and variations to the structures and methods recited above and shown in the drawings are possible without departing from the scope or spirit of the above disclosure and the following claims. The embodiments were chosen and described in order to explain the principles of the invention and their practical application so as to enable others skilled in the art to make and utilize the invention and various embodiments and with various modifications as are suited to the particular use contemplated. Alternative embodiments will become apparent to those skilled in the art to which the present invention pertains without departing from its spirit and scope.

The invention claimed is:

1. A bone plate system for fixation of bone, the system comprising:
 a) a bone plate comprising a bone contacting surface, an upper surface, and a first opening extending between the bone contacting surface and the upper surface, the first opening comprising a lower portion, a non-threaded upper portion, and a threaded portion converging towards the lower portion, the threaded portion comprising threads of a first material, the lower portion comprising a smallest diameter of the first opening; and
 b) a first fastener comprising a head at least partially comprising a polymeric material that is softer than the first material,
 wherein, when the first fastener is inserted into the first opening, the threads of the first opening form threads in the polymeric material on the head of the first fastener to secure the first fastener in place at one of a plurality of possible angles within the first opening.

2. The system of claim 1, wherein the polymeric material comprises polyethylene.

3. The system of claim 1, further comprising a second fastener comprising a shaft for engaging bone and a head having fins, wherein, when the second fastener is inserted in the first opening, the fins on the head of the second fastener engage the threads of the first opening to secure the second fastener in place at one of a plurality of possible angles within the first opening.

4. The system of claim 1, wherein the first opening comprises an axis and wherein the first opening is asymmetrical about the axis.

5. The system of claim 1, wherein the upper portion is adjacent the upper surface of the plate comprises a substantially frustoconical-shaped and the lower portion is adjacent the bone contacting surface of the plate and comprises at least some of the threads.

6. The system of claim 5, wherein the supper portion of the first opening comprises a ramp and a generally spherical-shaped recessed portion.

7. The system of claim 5, wherein the lower portion of the first opening is tapered.

8. The system of claim 1, wherein the bone plate comprises a plurality of first openings.

9. The system of claim 1, wherein the bone plate further comprises a second opening extending between the bone contacting surface and the upper surface, wherein the second opening comprises a plurality of protruding fins.

10. A method of reducing a fracture of a bone, the method comprising:
 a) reducing the fracture to bring bone fragments in close apposition;
 b) providing a bone plate comprising a bone contacting surface, an upper surface, and openings extending between the bone contacting and upper surfaces, wherein at least some of the openings comprise threads, the at least some of the openings comprising a lower portion, a non-threaded upper portion, and a threaded portion converging towards the lower portion, the lower portion comprising a smallest diameter of the at least some of the openings;
 c) compressing the bone plate against the bone with a first fastener to hold the fracture reduction; and
 d) inserting a second fastener into one of the openings in the bone plate comprising threads,
 wherein the second fastener comprises a head at least partially comprising a polymeric material, and wherein, when the second fastener is inserted into the at least some of the openings comprising threads, the threads of the opening form threads in the polymeric material of the head of the second fastener to secure the second fastener in place at one of a plurality of possible angles relative to the bone plate.

11. The method of claim 10, wherein the first fastener is inserted before the second fastener.

12. The method of claim 10, wherein the first fastener is inserted after the second fastener.

13. A method of reducing a fracture of a bone, the method comprising:
 a) providing a bone plate comprising a bone-contacting surface, an upper surface, and a first and second opening extending between the bone-contacting and upper surfaces, wherein the first opening comprises a lower portion, a non-threaded upper portion, and a threaded portion converging towards the lower portion, the lower portion comprising a smallest diameter of the first opening;

b) providing a first fastener comprising a head, wherein the head comprises a polymeric material;

c) inserting the first fastener through the first opening and on a first side of the fracture, wherein the threads of the first opening form threads in the polymeric material on the head of the first fastener to secure the first fastener in place at one of a plurality of possible angles within the first opening; and d) inserting a second fastener through the second opening and into engagement with the bone on a second side of the fracture opposite the first side to adjust positioning of the bone and surrounding tissue.

14. A bone plate system for fixation of a bone, the system comprising:

a) a bone plate comprising an upper surface, a bone contacting surface, and a first opening extending between the bone contacting surface and the upper surface, wherein the first opening comprises a substantially frustoconical-shaped top portion adjacent the upper surface of the plate, a bottom portion adjacent the bone contacting surface of the plate, and a threaded portion converging towards the bottom portion and comprising threads made of a first material, wherein the top portion comprises a non-threaded portion and wherein the bottom portion comprises a smallest diameter of the first opening; and b) a first fastener comprising a head and shaft for engaging bone, wherein a portion of the head comprises a polymeric material that is softer than the first material, wherein, when the first fastener is inserted into the first opening, the threads of the first opening form threads in the polymeric material of the head of the fastener.

15. The system of claim 14, wherein the polymeric material comprises polyethylene.

16. The system of claim 14, wherein the first material comprises titanium, stainless steel, cobalt chrome, plastic, polyetheretherketone, polyethylene, ultra high molecular weight polyethylene, resorbable polylactic acid, polyglycolic acid, or combinations thereof.

17. The system of claim 14, further comprising a second fastener comprising a shaft for engaging bone and a head comprising threads, wherein, when the second fastener is inserted into the first opening, the threads on the head of the second fastener engage with the threads of the first opening.

18. The system of claim 14, further comprising a second fastener comprising a shaft for engaging bone and a head comprising a spherical portion, wherein, when the second fastener is inserted into the first opening, the spherical portion of the head abuts the top portion of the first opening.

19. The system of claim 14, wherein the first opening comprises an axis and wherein the first opening is asymmetrical about the axis.

20. The system of claim 14, wherein the first opening comprises an axis and wherein the top portion comprises a ramp extending from the upper surface at an angle to the axis.

21. The system of claim 14, wherein the top portion of the first opening further comprises a generally spherical-shaped recessed portion.

22. The system of claim 14, wherein the top portion of the first opening further comprises a threaded portion.

23. The system of claim 14, wherein the bottom portion of the first opening is tapered.

24. The system of claim 14, wherein the bone plate comprises a plurality of first openings.

25. The system of claim 14, wherein the bone plate further comprises a second opening comprising a non-threaded opening.

26. The system of claim 25, wherein the bone plate comprises a plurality of second openings.

* * * * *

UNITED STATES PATENT AND TRADEMARK OFFICE
CERTIFICATE OF CORRECTION

PATENT NO. : 8,105,367 B2  
APPLICATION NO. : 12/484527  
DATED : January 31, 2012  
INVENTOR(S) : Gene Edward Austin et al.

Page 1 of 1

It is certified that error appears in the above-identified patent and that said Letters Patent is hereby corrected as shown below:

On the front page, "(75) Inventors:", replace "Southave" with --Southaven--.

At Col. 8, line 49, replace "an a" with --as a--.

At Col. 12, line 30, replace "threadform" with --thread form--.

At Col. 16, line 37, replace "threat" with --treat--.

At Claim 5, Col. 18, line 17, replace "plate" with --plate and--.

At Claim 6, Col. 18, line 21, replace "supper" with --upper--.

Signed and Sealed this  
Tenth Day of July, 2012

David J. Kappos  
*Director of the United States Patent and Trademark Office*